US012702403B2

(12) United States Patent
Wiebe et al.

(10) Patent No.: US 12,702,403 B2
(45) Date of Patent: Aug. 11, 2026

(54) VESSEL CLOSURE DEVICES AND METHODS

(71) Applicant: NeuroFine Corp., Miramar, FL (US)

(72) Inventors: Quinton Wiebe, Davie, FL (US); Brad D. Aurilia, Coral Springs, FL (US); Nicholas Shattuck, Lauderhill, FL (US); Daniel Sablyak, Sunrise, FL (US)

(73) Assignee: Neuro Fine Corp., Miramar, FL (US)

( * ) Notice: Subject to any disclaimer, the term of this patent is extended or adjusted under 35 U.S.C. 154(b) by 0 days.

(21) Appl. No.: 18/669,040

(22) Filed: May 20, 2024

(65) Prior Publication Data

US 2024/0307053 A1 Sep. 19, 2024

Related U.S. Application Data

(62) Division of application No. 17/546,947, filed on Dec. 9, 2021, now Pat. No. 12,035,905.

(60) Provisional application No. 63/191,017, filed on May 20, 2021, provisional application No. 63/124,400, filed on Dec. 11, 2020.

(51) Int. Cl.

| | |
|---|---|
| ***A61B 17/04*** | (2006.01) |
| ***A61B 17/062*** | (2006.01) |
| *A61B 17/00* | (2006.01) |
| *A61B 17/06* | (2006.01) |

(52) U.S. Cl.

CPC ...... *A61B 17/0469* (2013.01); *A61B 17/0482* (2013.01); *A61B 17/062* (2013.01); *A61B 2017/00367* (2013.01); *A61B 17/0057* (2013.01); *A61B 17/0491* (2013.01); *A61B 2017/0496* (2013.01); *A61B 17/06066* (2013.01)

(58) Field of Classification Search

CPC ............ A61B 17/0469; A61B 17/0482; A61B 17/062; A61B 17/0057; A61B 17/0491; A61B 17/06066; A61B 2017/00367; A61B 2017/0496; A61B 2017/00663; A61B 2017/0472

See application file for complete search history.

(56) References Cited

U.S. PATENT DOCUMENTS

| | | | | |
|---|---|---|---|---|
| 6,641,592 | B1 | 11/2003 | Sauer | |
| 7,341,595 | B2 | 3/2008 | Hinchliffe et al. | |
| 7,449,024 | B2 * | 11/2008 | Stafford ............ | A61B 17/0469 606/139 |
| 9,895,146 | B1 | 2/2018 | Al-Jazaeri | |

(Continued)

OTHER PUBLICATIONS

International Search Report and Written Opinion in PCT/US2021/062667, 10 pages. Mar. 2, 2022.

(Continued)

*Primary Examiner* — Kathleen S Holwerda
*Assistant Examiner* — James R McGinnity

(57) ABSTRACT

A vessel closure device comprising a proximal end includes a first actuator, a distal end including a suturing mechanism, and first and second needles associated with the suturing mechanism. At least one of the first and second needles is coupled to the first actuator. The suturing mechanism is activated within the vessel through an opening in the wall of the vessel. The first and second needles are directed through the vessel wall adjacent to the opening to direct a tensile member adjacent to the opening for closing and sealing the opening.

5 Claims, 23 Drawing Sheets

(56) References Cited

U.S. PATENT DOCUMENTS

| | | | | |
|---|---|---|---|---|
| 2002/0016602 | A1 | 2/2002 | Li | |
| 2004/0097978 | A1 | 5/2004 | Modesitt et al. | |
| 2006/0069397 | A1 | 3/2006 | Nobles et al. | |
| 2008/0269786 | A1 | 10/2008 | Nobles et al. | |
| 2010/0030242 | A1* | 2/2010 | Nobles | A61B 17/0469 606/147 |
| 2010/0145364 | A1 | 6/2010 | Keren et al. | |
| 2012/0029532 | A1* | 2/2012 | Hodgkinson | A61B 17/0057 606/139 |
| 2012/0035623 | A1* | 2/2012 | Bagaoisan | A61B 17/0482 606/144 |
| 2012/0071901 | A1 | 3/2012 | Heneveld | |
| 2013/0178872 | A1 | 7/2013 | Shriver | |
| 2013/0310853 | A1* | 11/2013 | Zaugg | A61B 17/0469 606/232 |
| 2014/0249552 | A1 | 9/2014 | Tang et al. | |
| 2017/0071599 | A1 | 3/2017 | Malkowski | |
| 2018/0228478 | A1 | 8/2018 | Fortson | |
| 2019/0008506 | A1 | 1/2019 | Kurd et al. | |
| 2020/0093478 | A1 | 3/2020 | Caffes et al. | |

OTHER PUBLICATIONS

International Search Report and Written Opinion in PCT/US2021/062671, 10 pages. Mar. 2, 2022.

Terumo Medical Corporation, Angio Seal Vascular Closure Device Online Brochure, Terumo Medical Corporation, Somerset, New Jersey, 5 pages. 2022.

Abbott, Perclose Prostyle Suture-Mediated Closure and Repair System Online Brochure, Abbott, Abbott Park, Illinois, 24 pages. 2022.

Teleflex. Manta Vascular Closure Device Online Brochure, Wayne, Pennsylvania, 8 pages. 2020.

Veryan Medical, Celt ACD Vascular Closure Device Online Product Description, Veryan Medical, Horsham, West Sussex, United Kingdom, 3 pages. 2022.

Syed M. Hussein Md, Prospective Evaluation of the CELT Arterial Closure Device in an Outpatient Based Catheterization Laboratory Presentation, Champaign, Illinois, 14 pages. Apr. 18, 2019.

Cordis, Mynx Control Vascular Closure Device Step-by-Step Guide Online Brochure, Cordis, Santa Clara, California, 2 pages. 2021.

U.S. Patent and Trademark Office, International Preliminary Report on Patentability in related PCT/US2021/062671, Jul. 13, 2023.

U.S. Patent and Trademark Office, International Preliminary Report on Patentability in related PCT/US2021/062667, Jul. 25, 2023.

EP Application No. 21904419.5, Extended European Search Report mailed May 24, 2024, Applicant: Neurofine Corp., 9 pages.

EP Application No. 21904423.7, Extended European Search Report mailed May 23, 2024, Applicant: Neurofine Corp., 9 pages.

U.S. Appl. No. 17/546,947, Final Office Action mailed Oct. 23, 2023, Inventor: Wiebe et al., 20 pages.

U.S. Appl. No. 17/546,947, Non-Final Office Action mailed May 17, 2023, Inventor: Wiebe et al., 20 pages.

U.S. Appl. No. 17/546,958, Final Office Action mailed Nov. 7, 2023, Inventor: Shattuck et al., 25 pages.

U.S. Appl. No. 17/546,958, Non-Final Office Action mailed May 22, 2023, Inventor: Shattuck et al., 17 Pages.

U.S. Appl. No. 18/751,896, Non-Final Office Action mailed Feb. 27, 2026, Inventor: Shattuck et al., 12 pages.

* cited by examiner 10
12
23
44
46
28b
28a
20
31
28c
32
44
46
25
22b
22
22a
43

14
52
48
26
52
24
30
40a
10
42a
40
42
40b
16

10
12
23
44
46
28b
28a
20
31
28c
32
44
46
25
22b
22a
22

24
52
14
48
26
40a
52
30
42a
10
40
42
40b
16

10
12
44
46
28b
28a
20
31
28c
32
44
46
25
22b
22
22a 24
52
14
26
52
50
30
50
10
40a
40
48
42a
40b
42
16

VESSEL CLOSURE DEVICES AND METHODS

CROSS REFERENCE TO RELATED APPLICATIONS

This application is a divisional of U.S. patent application Ser. No. 17/546,947, filed Dec. 9, 2021 (pending), which claims the priority of U.S. Provisional Patent Application Ser. No. 63/124,400, filed Dec. 11, 2020 (expired), and U.S. Provisional Patent Application Ser. No. 63/191,017, filed May 20, 2021 (expired), the disclosures of which are incorporated herein by reference in their entirety.

This application is also generally related to the subject matter disclosed in U.S. patent application Ser. No. 17/546,958, filed Dec. 9, 2021 (pending), PCT Application Serial No. PCT/US2021/062667, filed Dec. 9, 2021 (expired), and PCT Application Serial No. PCT/US2021/062671, filed Dec. 9, 2021 (expired), the disclosures of which are incorporated herein by reference in their entirety.

TECHNICAL FIELD

The present invention generally relates to closure devices and methods for sealing punctures or other openings in blood vessels, such as the common carotid artery made during a direct access approach for neurological therapy. The devices and methods may be used in the course of other therapies or surgical procedures as well.

BACKGROUND

Vascular access for neuro-therapy is traditionally performed through the femoral artery or radial access approaches. For vascular access to the brain using a traditional approach, neuro-therapy devices must navigate through lengthy tortuous segments of the anatomy to gain access to the therapeutic site. The Direct Carotid Artery Puncture (DCP) method for accessing the common carotid artery allows doctors quicker access to the brain and eliminates the need for devices that must traverse the typical femoral interventional track. Given these benefits, it would be further advantageous to seal the puncture from this DCP method in a more efficient and effective manner.

To close and seal a DCP, doctors currently may apply a suture manually prior to the access or may simply apply direct pressure to the site after intervention until the vessel seals itself. The latter method relies on blood coagulation at the puncture site. Therefore, the time period necessary for closing the puncture with direct pressure may be quite lengthy. Also, this method may be less than effective because of the lack of suitable anatomy in the vicinity of the common carotid artery against which the pressure may be applied. Moreover, the common carotid artery carries blood at a high pressure (100 to 200 mmHg) which further complicates the ability to effectively close the carotid puncture with current methods.

SUMMARY

Generally, a vessel closure device is provided and includes a proximal end with a first actuator, a distal end including a suturing mechanism, and first and second needles associated with the suturing mechanism. At least one of the first and second needles is coupled to the first actuator. The suturing mechanism is activated within the vessel through an opening in the wall of the vessel and the first and second needles are directed through the vessel wall adjacent to the opening to direct a tensile member adjacent to the opening for closing and sealing the opening.

In some embodiments, the vessel closure device may have a second actuator coupled to the suturing mechanism for moving the suturing mechanism into an activated orientation. The suturing mechanism may have a pivotal element capable of being moved into a deployed orientation within the vessel by the second actuator.

In alternate or additional aspects, the vessel closure device may include a handle and an elongate shaft coupled between the handle and the suturing mechanism. The first actuator may be carried by the handle. The first actuator of the vessel closure device may be spring-biased into a position for retracting at least one of the first and second needles.

In alternate embodiments, the vessel closure device may include a second actuator and the first needle may be coupled to the first actuator and the second needle may be coupled to the second actuator. The second actuator may be spring-biased into a position for retracting the second needle.

In another illustrative embodiment, a vessel closure device includes a proximal end with a handle with first and second actuators. The device also includes first and second needles, where at least one of the first and second needles is coupled to the first actuator. A distal end of the device includes a suturing mechanism and the suturing mechanism includes a pivotal element coupled to the second actuator. The pivotal element is activated within the vessel through an opening in the wall of the vessel while the pivotal element is in a first orientation. The second actuator is used to reorient the pivotal element into a second, deployed orientation. The first and second needles are directed through the vessel wall adjacent to the opening with the first actuator to direct a tensile member adjacent to the opening for closing and sealing the opening.

In some embodiments, an elongate shaft may be coupled between the handle and the suturing mechanism, and the first actuator and the second actuator may be carried by the handle of the vessel closure device. The first actuator may be spring-biased into a position for retracting at least one of the first and second needles. The second actuator may be spring-biased into a position for moving the pivotal element into the first orientation.

In some embodiments, the vessel closure device may include a third actuator with the first needle coupled to the first actuator and the second needle coupled to the third actuator. The third actuator may be spring-biased into a position for retracting the second needle.

In alternate or additional aspects, the deployed orientation of the vessel closure device may be angled. The suturing mechanism may include a flexible coupling member having first and second ends with the first end being capable of coupling to the first needle and the second end being capable of coupling to the second needle. The first needle of the vessel closure device may include a detachable tip coupled to the tensile member. The vessel closure device include at least one tab coupled to the handle configured to accommodate a user's finger.

In alternate or additional aspects, the vessel may be a blood vessel and the vessel closure device may include an introducer sheath through which the suturing mechanism is directed into the blood vessel. The sheath may then be withdrawn from the blood vessel with the suturing mechanism remaining in the blood vessel thereby inhibiting blood from exiting the blood vessel through the opening.

In another illustrative embodiment, a vessel closure device for closing and sealing an opening in a blood vessel includes a suturing mechanism deployable into the vessel interior, at least one needle and a tensile member engaged with the suturing mechanism for closing the opening, and an introducer sheath through which the suturing mechanism is directed to enter the opening prior to closing the opening.

A method of closing an opening in a vessel is provided and includes directing a suturing mechanism through the opening into the vessel interior. A tensile member is directed through the vessel wall adjacent to the opening using the suturing mechanism. The suturing mechanism is withdrawn and the tensile member is tightened to close the opening in the vessel.

The method may include additional or alternative steps or features. For example, directing the tensile member through the vessel wall may further include directing at least one needle through the vessel wall. The vessel, for example, may be a blood vessel, and the method may include directing an introducer sheath into an opening in the blood vessel and directing the suturing mechanism through the introducer sheath and into the interior of the blood vessel. Withdrawing the introducer sheath from the blood vessel with the suturing mechanism remaining in the blood vessel may inhibit blood from exiting the blood vessel through the opening. A pivotal element of the suturing mechanism may be activated into a deployed orientation after the suturing mechanism is positioned within the interior of the vessel. The deployed orientation may be an angled orientation. The suturing mechanism may include a flexible coupling member with first and second ends, and the method may include coupling a first needle to the first end and a second needle to the second end of the coupling member. The method may further include retracting the first and second needles and pulling the tensile member through the vessel wall.

DETAILED DESCRIPTION

The device disclosed herein generally allows a single-suture closure of a blood vessel, such as the common carotid artery or another vessel, via a minimally invasive percutaneous approach. There are various non-limiting aspects that may be used alone or in any desired combination. The suturing device may be tracked through an introducer sheath thereby allowing an internal exchange of the suturing device and the introducer sheath. This will inhibit (that is, eliminate, or at least substantially reduce), blood loss normally experienced during a typical device exchange as a result of the high blood pressures found in the common carotid artery. These pressures may be 100 mmHg to 200 mmHg or more. In comparison, typical arterial pressures in a femoral or wrist exchange are in the range of 80 mmHg to 160 mmHg. The suturing device may generally include a proximally located handle, suture needles, sutures or other tensile members, suture transfer mechanisms and, optionally, a blood flow visual indicator. As used herein to describe various embodiments from the perspective of a user of a suturing device, "proximal" may refer to a direction generally towards the user of the device, while "distal" may refer to a direction generally away from the user of the device. The sutures may be percutaneously routed through the dermis skin layer and the vessel wall without affecting the epidermis or outer skin layer.

Figure 1:
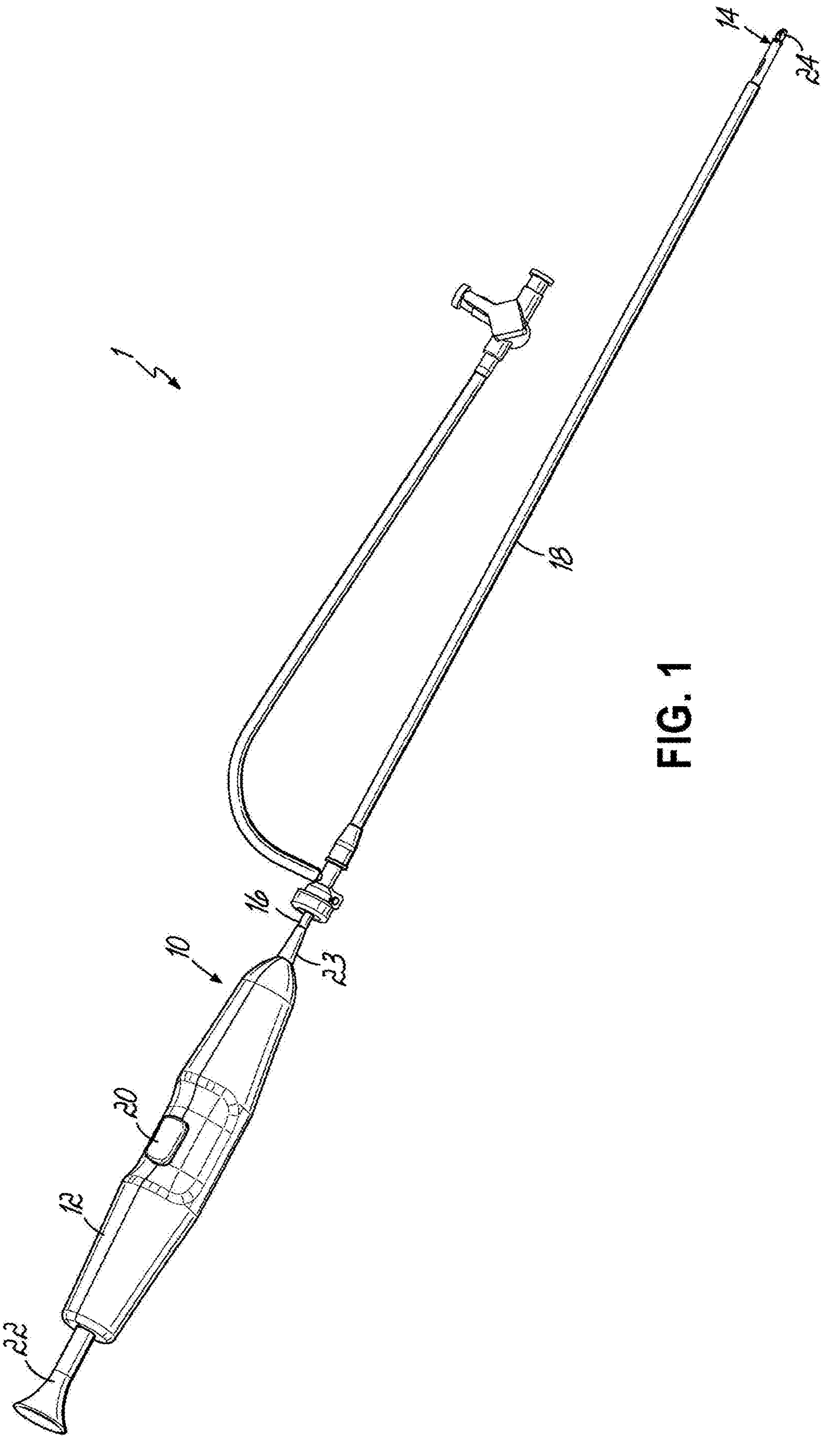
FIG. 1 is a perspective view of an exemplary suturing device with an introducer sheath.
Figure 2:
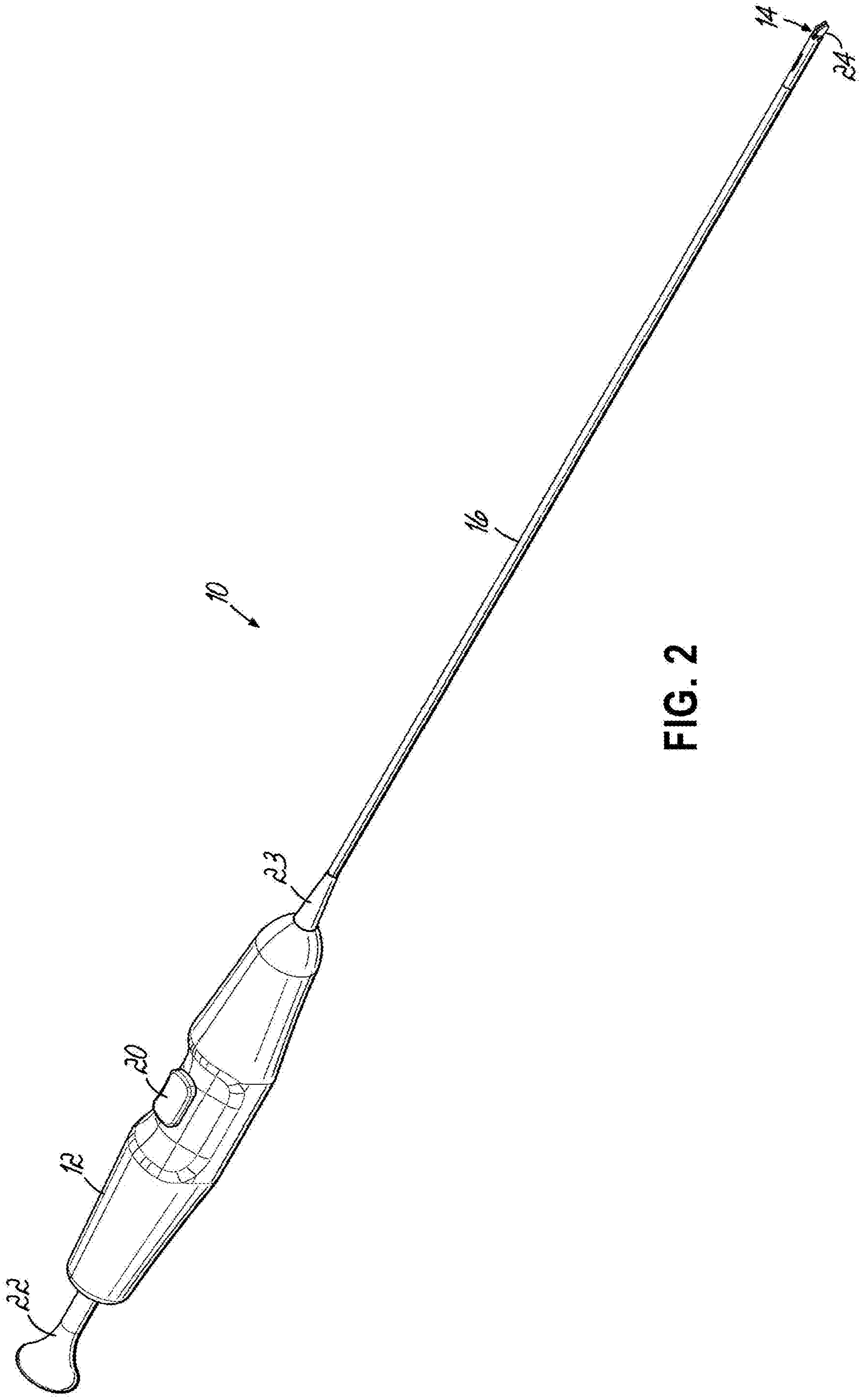
FIG. 2 is an alternate perspective view of the exemplary suturing device of FIG. 1 without the introducer sheath.

FIGS. 1 and 2 illustrate a first exemplary embodiment of a system 1 that includes a suturing device 10. The suturing device 10 generally includes a handle 12 at a proximal end and a suturing mechanism 14 at the distal end. As used herein, "suture", "suturing" and similar forms of these terms mean any flexible tensile element or member regardless of form or material and suitable for approximating tissue. As used herein, "tensile member" may be a mono-filament suture, a multi-filament suture, a metallic suture, or any other suitable tensile member. An elongate, narrow shaft 16 extends between the handle 12 and the suturing mechanism 14. The system 1 further includes an introducer sheath 18 through which the shaft 16 is directed during a suturing procedure as further described below. The handle 12 includes one or more actuating mechanisms necessary for operating the suturing mechanism 14 and the suturing needles (described below). In this exemplary embodiment, the actuating mechanisms include a sliding actuator 20 that operates the suturing mechanism 14 and a plunger actuator 22 that operates the suturing needles. While these actuators are shown and described as manually driven, one or more of the actuators may be motorized, mechanically leveraged or assisted in other manners. A strain relief 23 is fixed generally between the relatively rigid handle 12 and the more flexible shaft 16 to more evenly distribute forces between the handle 12 and the shaft 16.

Figure 2A:
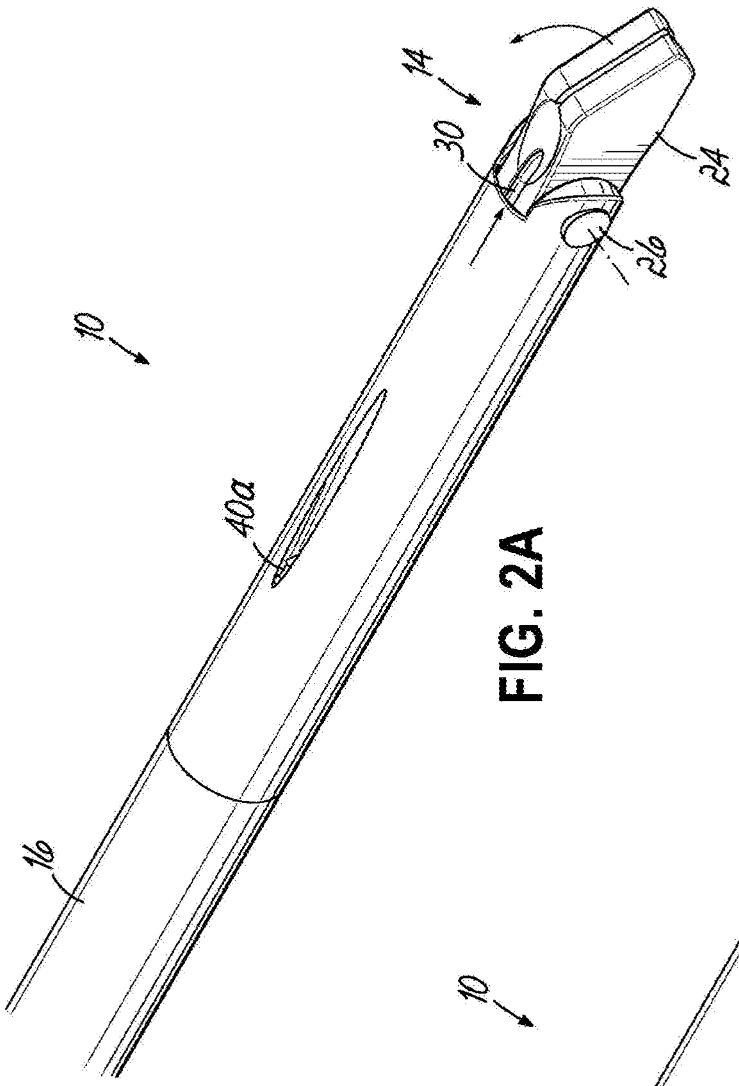
FIGS. 2A and 2B are perspective views of the distal end of the exemplary suturing device of FIGS. 1 and 2, and specifically, a shaft and suturing mechanism.
Figure 2B:
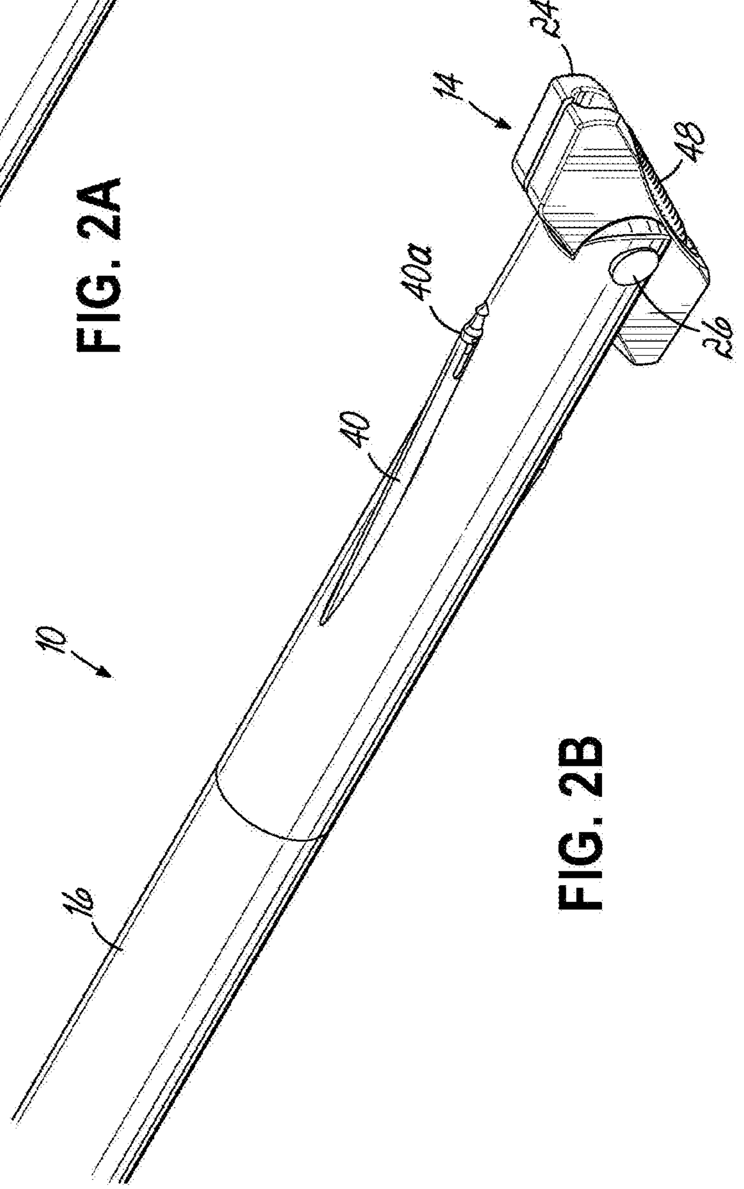
Figure 2C:
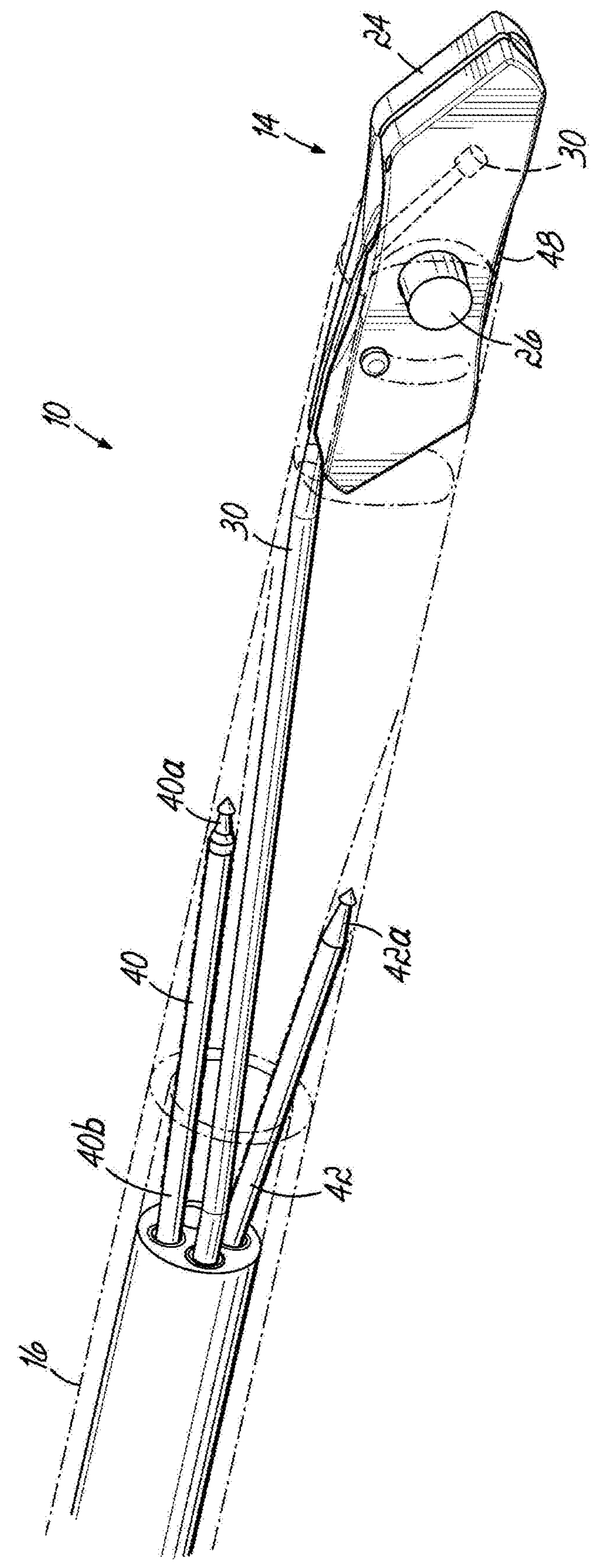
FIG. 2C is a detailed view of the distal end of the shaft and suturing mechanism of FIGS. 2A and 2B.

FIGS. 2A and 2B are perspective views of the distal end of the shaft 16 and specifically, the suturing mechanism 14. FIG. 2C is a detailed view of the distal end of the shaft 16 and suturing mechanism 14. The suturing mechanism 14 includes a pivotal element 24. This pivotal element 24 is secured to the distal end of the shaft 16 by a pivot 26 that allows the pivotal element 24 to pivot from an orientation, shown in FIG. 2A, that essentially aligns the lengthwise extent of the pivotal element 24 with the shaft 16 to an orientation that is transverse to the lengthwise axis of the shaft 16. As will become apparent from the description to follow, the transverse orientation of the pivotal element 24 facilitates a suturing procedure from within a blood vessel. As used herein, the term "vessel", "blood vessel", "arteries", "veins", and similar forms of these terms mean any component of the circulatory system that transports blood throughout the human body. The aligned orientation of the pivotal element 24 shown in FIG. 2A is an insertion and removal orientation as will be understood from the description to follow. The position shown for the pivotal element 24 in FIG. 2B is attained by actuating the slide 20 as described below.

Figure 2D:
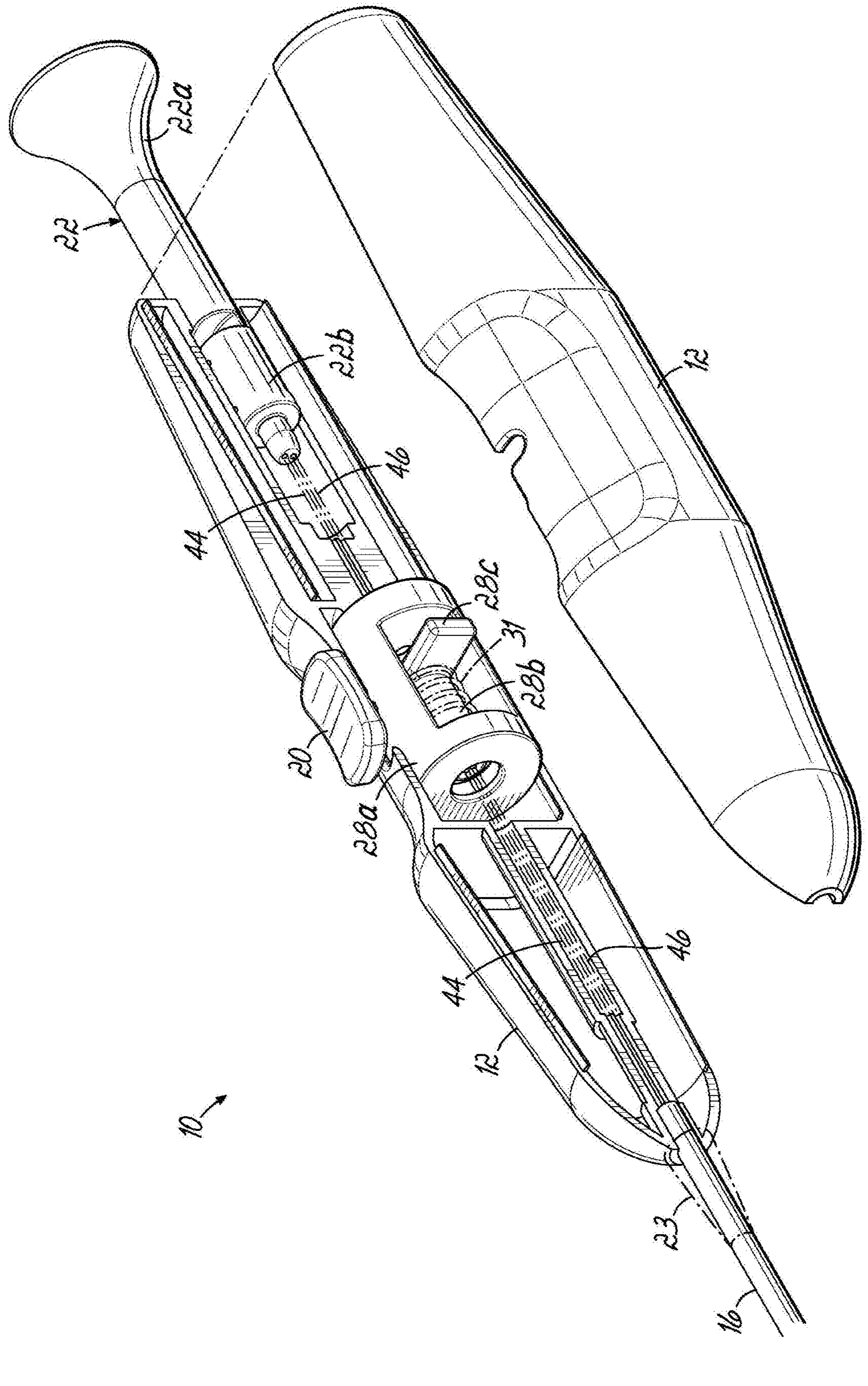
FIG. 2D is an exploded view illustrating a handle at the proximal end of the suturing device of FIGS. 1 and 2.
Figure 2E:
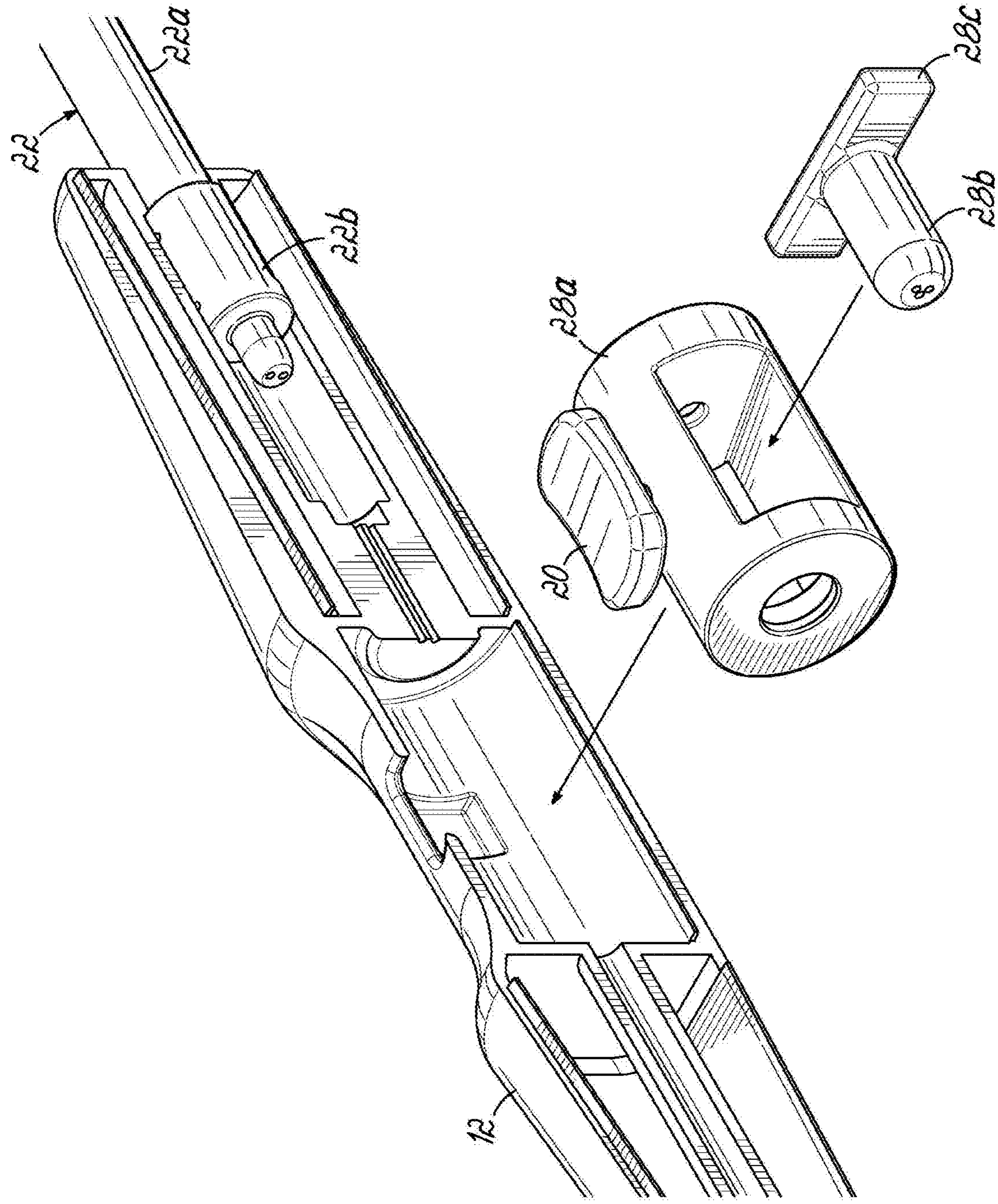
FIG. 2E is a further exploded view of the handle of FIG. 2D.
Figure 2F:
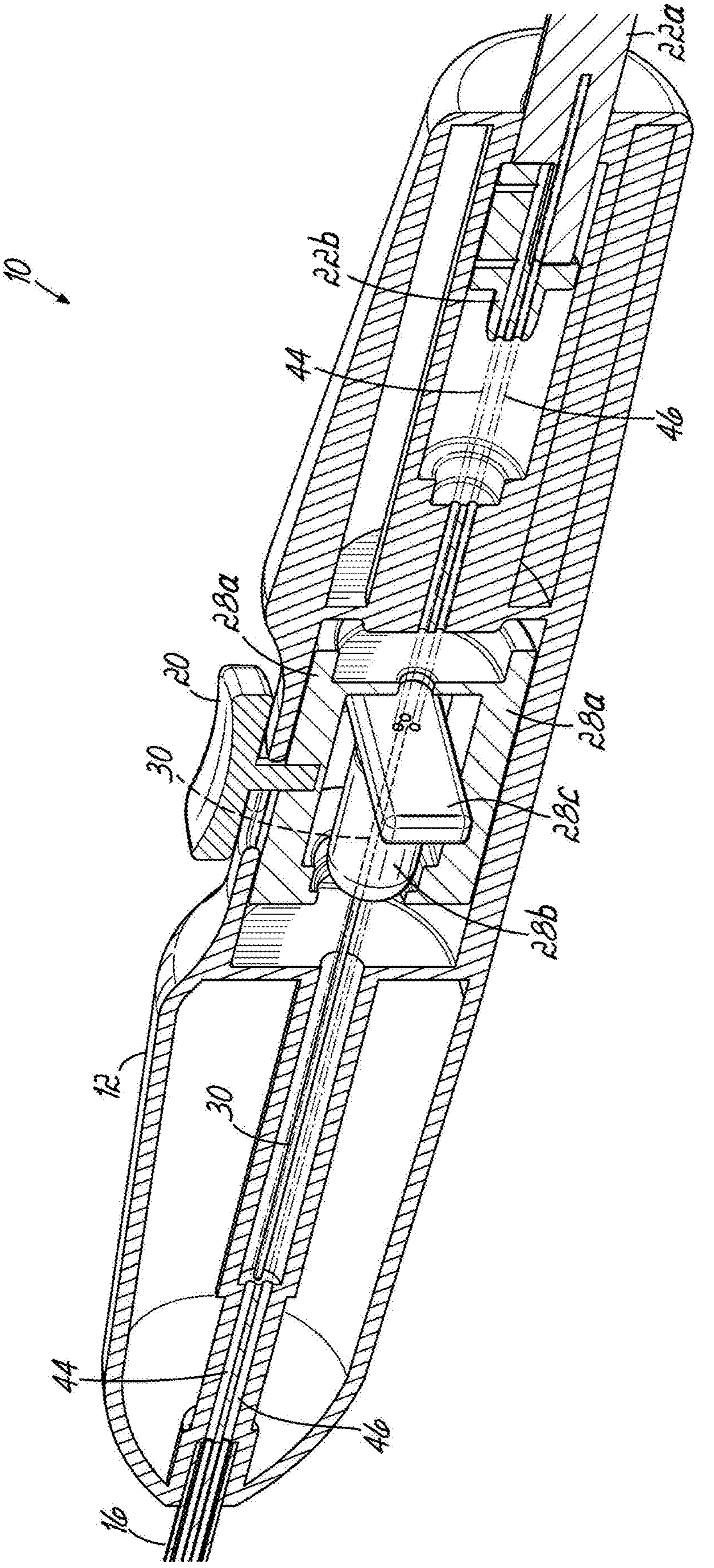
FIG. 2F is a cross-section illustrating the handle of FIG. 2D and its components.
Figure 2G:
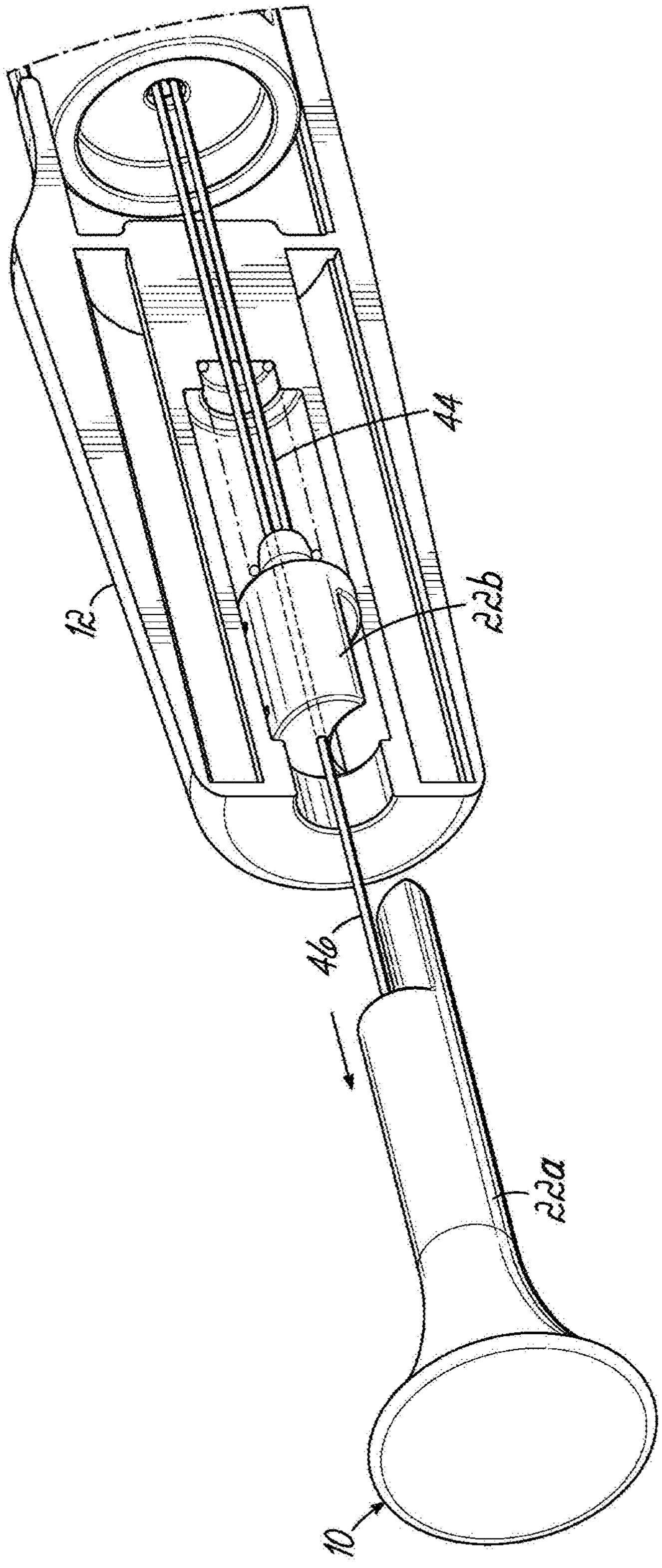
FIG. 2G is a cross-section of the proximal end of the handle of FIG. 2D.
Figure 3A:
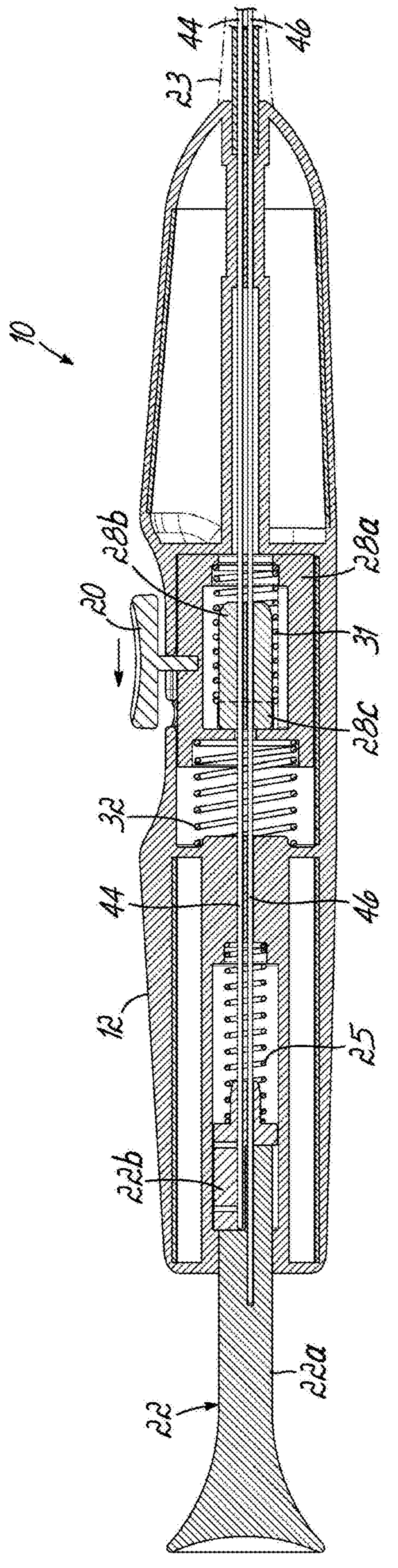
FIG. 3A is a cross-section view of the handle at the proximal end of the suturing device of FIGS. 1 and 2.
Figure 3B:
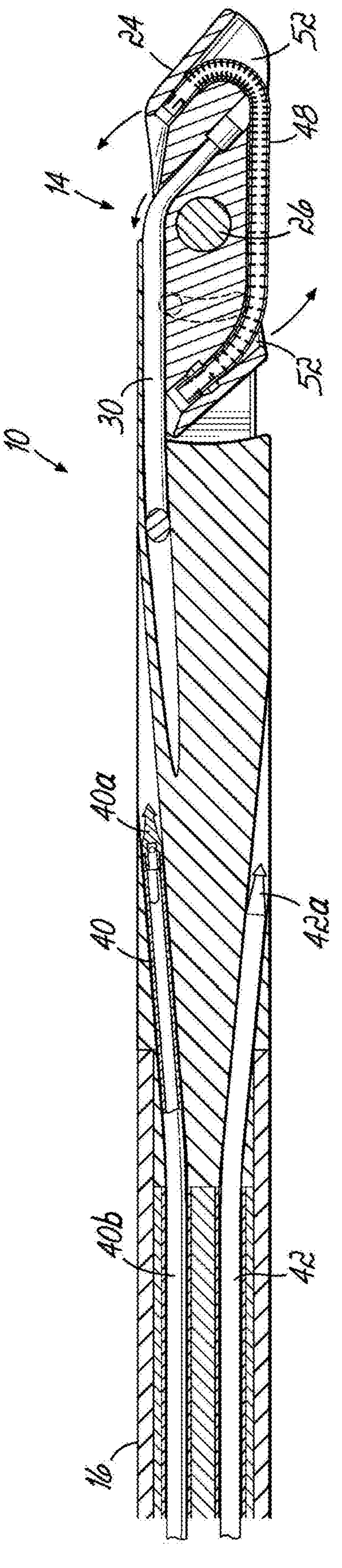
FIG. 3B is a cross-section view of the suturing mechanism of FIGS. 2A and 2B.

FIG. 2D is an exploded view illustrating the handle 12 and its components. FIG. 2E is a further exploded view of the handle 12 and its components. FIG. 2F is a cross-section illustrating the handle 12 and its components. FIG. 2G is a cross-section of the proximal end of the handle 12. FIG. 3A is a cross-section of the handle 12 at the proximal end of the device 10. FIG. 3B is a cross-section of the suturing mechanism 14 at the distal end of the device 10.

Referring to FIGS. 2D, 2E, 2F, 2G, and 3A, the sliding actuator 20 is fixed to an outer shuttle member 28*a*. The shuttle members 28*a* and 28*b* are independently movable, with the inner shuttle member 28*b* "floating" within the outer shuttle member 28*a*. A spring 31 is coupled between the shuttle members 28*a*, 28*b* and held between a cross leg portion 28*c* of the inner shuttle member 28*b* and an inner wall surface at the distal end of the outer shuttle member 28*a*. A second spring 32 is provided to bias the outer shuttle member 28*a* into its forward or distal position as shown in FIG. 3A. The plunger actuator 22 is a two-piece element comprised of a proximal plunger portion 22*a* and a distal plunger portion 22*b*. The plunger 22 is biased in the handle 12 by a coil spring 25, although other forms of biasing members may be used.

Referring to FIGS. 2D, 2E, 2F, 3A and 3B, an actuator wire 30 is fixed to an inner shuttle member 28*b* and is also fixed to the pivotal element 24 at the distal end of the device 10. The distal end of the actuation wire 30 is formed into the angled orientation shown in FIG. 3B. The distal end of the actuation wire 30 may be heat-set into the angled orientation shown in FIG. 3B, for example. The angled orientation of the actuation wire 30 provides a bias to hold the pivotal element 24 in lengthwise alignment with the lengthwise axis of the shaft 16 for insertion and removal. The pivotal element 24 includes a passage 52 with an elongate flexible coupling member 48 contained therein.

Referring to FIGS. 2C, 3A, and 3B, the distal end of the device 10 includes two needles 40, 42 which are either fully integral with or fixedly coupled to respective wires 44, 46. Needle 40 is a two-piece needle which has a needle tip 40*a* detachable from a needle body 40*b* by way of a friction fit, for example. Needle 42 has an integral (i.e., fixed) tip 42*a*. The word "integral" here encompasses fully integral constructions as well as constructions in which the tip 42*a* is fixedly (i.e., not "removably") coupled to the remainder of the integral needle 42. Elements 40, 44 and 42, 46 may be solid wire-like members or hollow (e.g., hypotubes). The wire-like or hypotube element 44 (coupled with two-piece needle 40) is fixed to the distal plunger portion 22*b*, while the wire or hypotube element 46 (coupled to the needle 42) is fixed to the proximal plunger portion 22*a*.

Figure 4A:
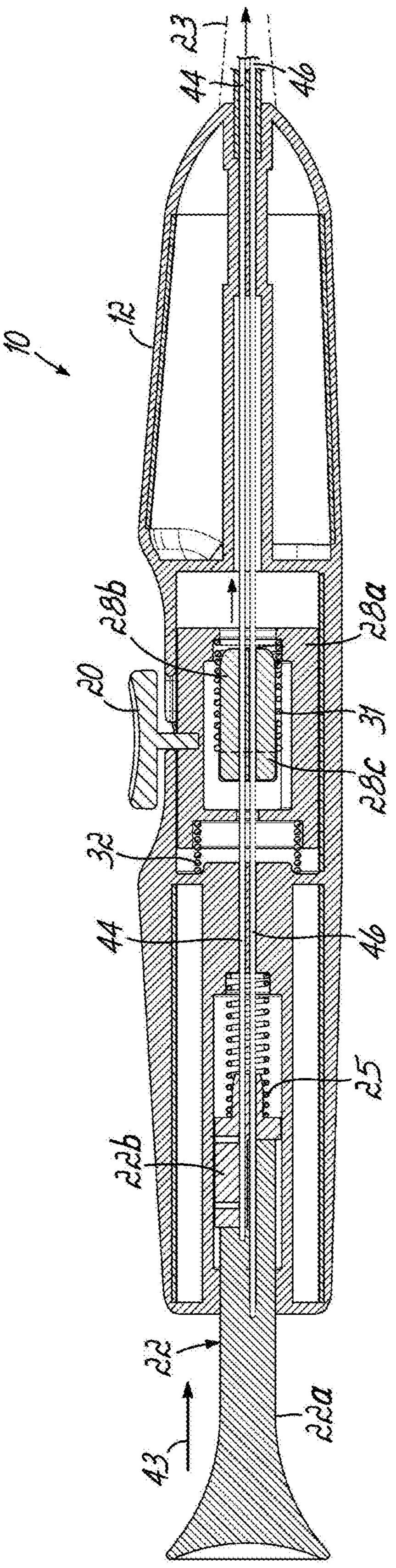
FIG. 4A is a cross-section view of the handle at the proximal end of the suturing device of FIGS. 1 and 2.
Figure 4B:
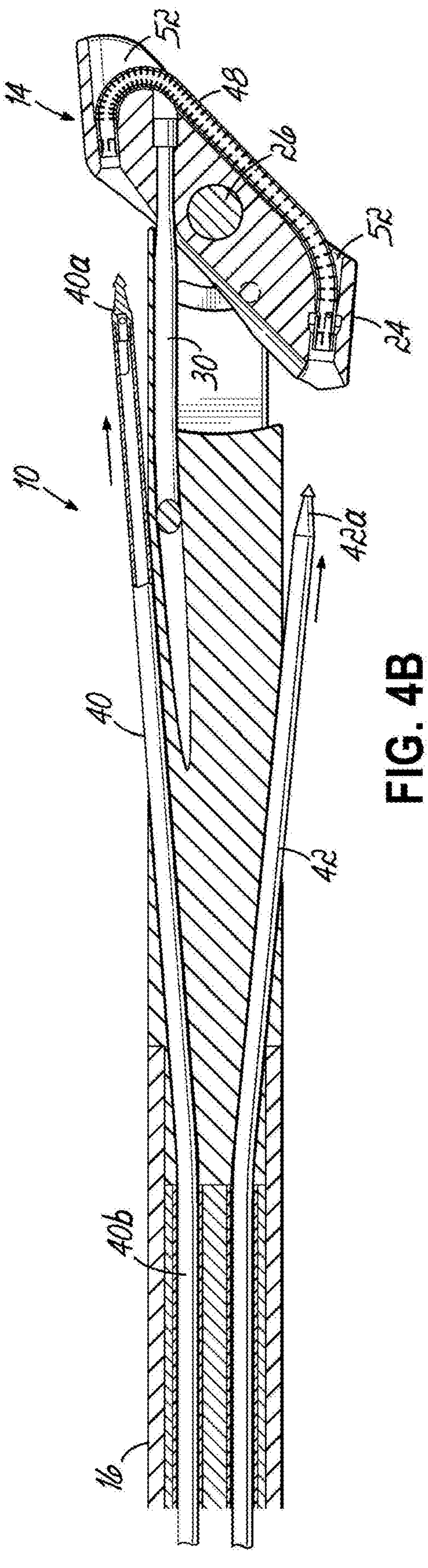
FIG. 4B is a cross-section view of the suturing mechanism of FIGS. 2A and 2B.
Figure 5A:
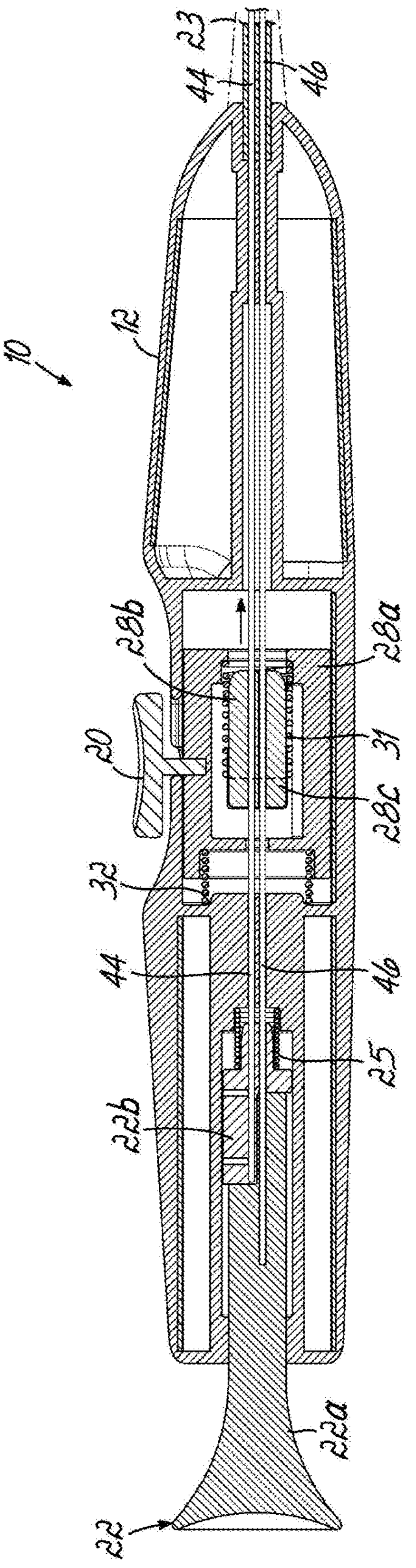
FIG. 5A is a cross-section view of the handle at the proximal end of the suturing device of FIGS. 1 and 2.
Figure 5B:
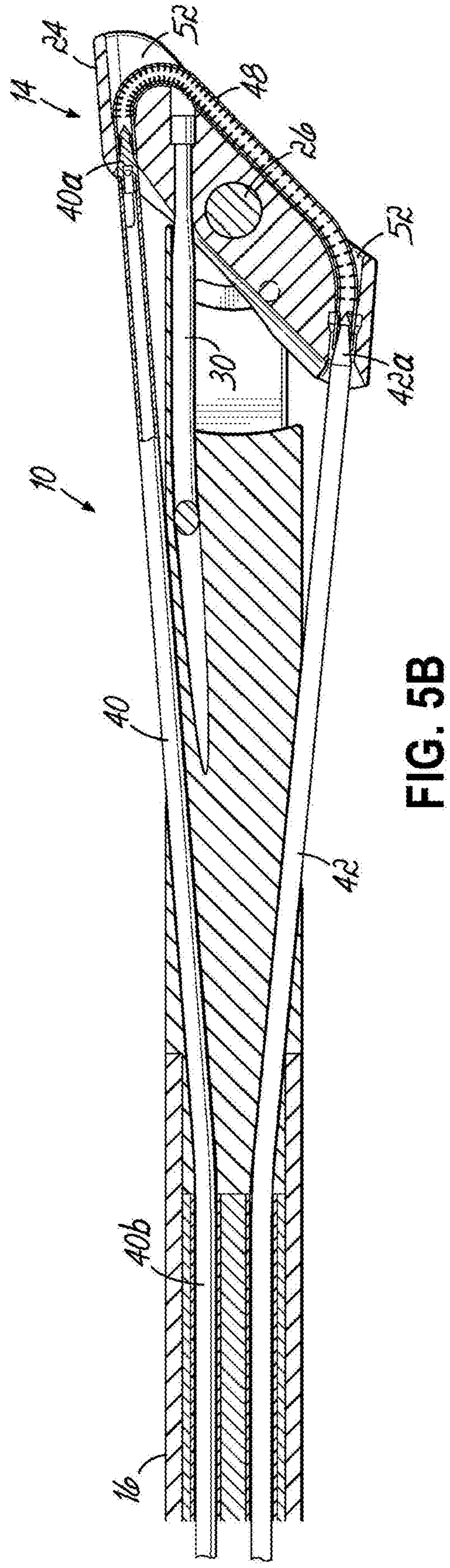
FIG. 5B is a cross-section view of the suturing mechanism of FIGS. 2A and 2B.
Figure 6A:
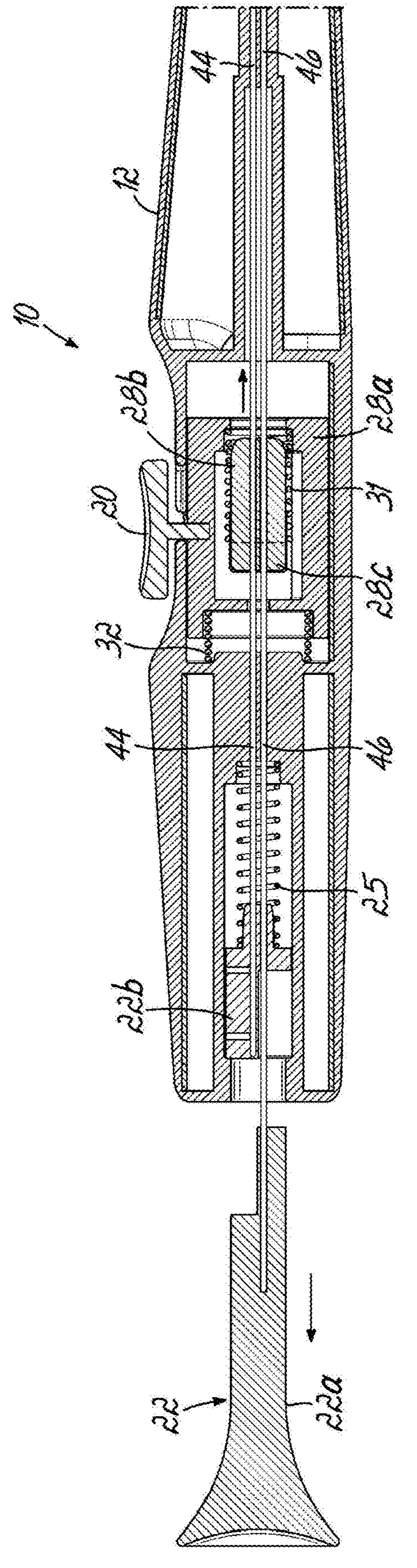
FIG. 6A is a cross-section view of the handle at the proximal end of the suturing device of FIGS. 1 and 2.
Figure 6B:
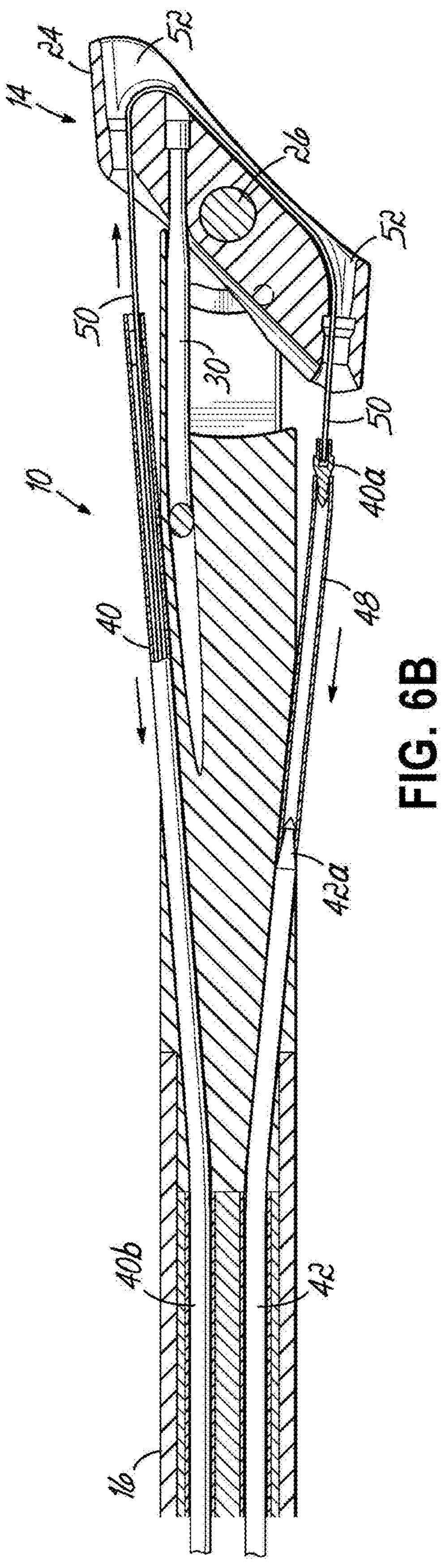
FIG. 6B is a cross-section view of the suturing mechanism of FIGS. 2A and 2B.

FIGS. 3A, 3B, 4A, 4B, 5A, 5B, 6A and 6B progressively illustrate additional structure and function or methodology of the device 10. FIGS. 4A and 4B are respective cross-sections of the handle 12 and the suturing mechanism 14 with the suturing mechanism 14 in a deployed orientation. FIGS. 5A and 5B are respective cross-sections of the handle 12 and the suturing mechanism 14 with needle tips 40*a*, 42*a* engaging and connecting with respective ends of the elongate flexible coupling member 48. FIGS. 6A and 6B are respective cross-sections of the handle 12 and the suturing mechanism 14.

Reference is now made to FIGS. 3A, 3B, 4A, 4B, 5A, 5B, 6A and 6B. As schematically illustrated in FIG. 3A, moving the slide actuator 20 in a rearward or proximal direction, will pull or move the outer shuttle member 28*a* in a rearward or proximal direction within the handle 12. Pulling or moving the slide actuator 20 in a proximal direction will activate the suturing mechanism 14, and pivot the pivotal element 24 from the insertion and removal orientation shown in FIG. 3B into the deployed orientation shown in FIG. 4B. Moving the outer shuttle member 28*a* proximally will also force the inner shuttle member 28*b* proximally.

The slide actuator 20 is then mechanically locked into position in a suitable manner, such as by being moved within a "J" or "L" slot in the handle 12 as shown best in FIGS. 9A and 10A further described below, for example. The shuttle members 28*a*, 28*b* are held in the positions shown in FIG. 4A with the pivotal element 24 in its deployed, angled orientation as shown in FIG. 4B. The pivotal element 24 is held in this deployed orientation against the bias of the spring 31 coupled between the shuttle members 28*a*, 28*b* as shown in FIGS. 4A through 6A.

Releasing or moving the slide actuator 20 in a forward or distal direction will allow the pivotal element 24 to pivot from the deployed orientation shown in FIG. 4B to the insertion and removal orientation shown in FIG. 3B. Spring 32 will bias the outer shuttle member 28*a* into its forward or distal position as shown in FIG. 3A. The angled orientation of proximal end of the actuation wire 30 provides additional bias to pivot the pivotal element 24 to the insertion and removal orientation. In this manner, the combined forces of spring 32 and formed portion of actuator wire 30 will force the wire 30, and thereby the pivotal element 24, into the position shown in FIG. 3B after the slide actuator 20 is unlocked and released in a forward or distal direction.

While the pivotal element 24 is in the deployed, angled orientation as shown in FIG. 4B, respective suture needles 40, 42 are deployed or moved in distal directions by depressing or pushing the proximal plunger 22 in a distal direction as indicated by the arrow 43 (FIG. 4A) and against the bias provided by the coil spring 25. For purposes of deploying the needles 40, 42 in a distal direction the plunger 22 is pushed in a distal direction (see arrow 43 in FIG. 4A). This simultaneously moves plunger portions 22*a*, 22*b* in the distal direction and moves needles 40, 42 in the distal direction (see FIGS. 4B and 5B). As further shown in FIG. 5B, upon pushing the plunger 22, the respective needle tips 40*a*, 42*a* engage and connect with respective ends of the elongate flexible coupling member 48. The needle tip 40*a* is fixed to an elongate tensile element or suture 50 (FIG. 6B). As the needle 42 is pulled rearwardly or in a proximal direction by pulling proximal plunger portion 22*a*, needle 42 will pull the flexible coupling member 48 through passage 52 in the pivotal element 24 and the flexible coupling member 48 will carry with it the released needle tip 40*a* and tensile element or suture 50. As shown in FIGS. 6A and 6B, needle body 40*b* will be retracted slightly by the spring-biased movement of distal plunger portion 22*b* when the plunger 22 is released and the proximal plunger portion 22*a* is pulled proximally. Specifically, the distal plunger portion 22*b* will move proximally (but remain within or attached to the handle 12) and thereby pull wire or hypotube 44 and needle body 40*b* a short distance with it due to the expansion of spring 25. The plunger 22 may be designed to prevent rotation of the plunger portions 22*a* and 22*b* about the longitudinal axis of the device 10. For example, portions 22*a* and 22*b* may have square cross sections as may the structures that interact with them to prevent rotation of these components within the handle 12 and allow only translation generally along the axis of the device 10.

Figure 7A:
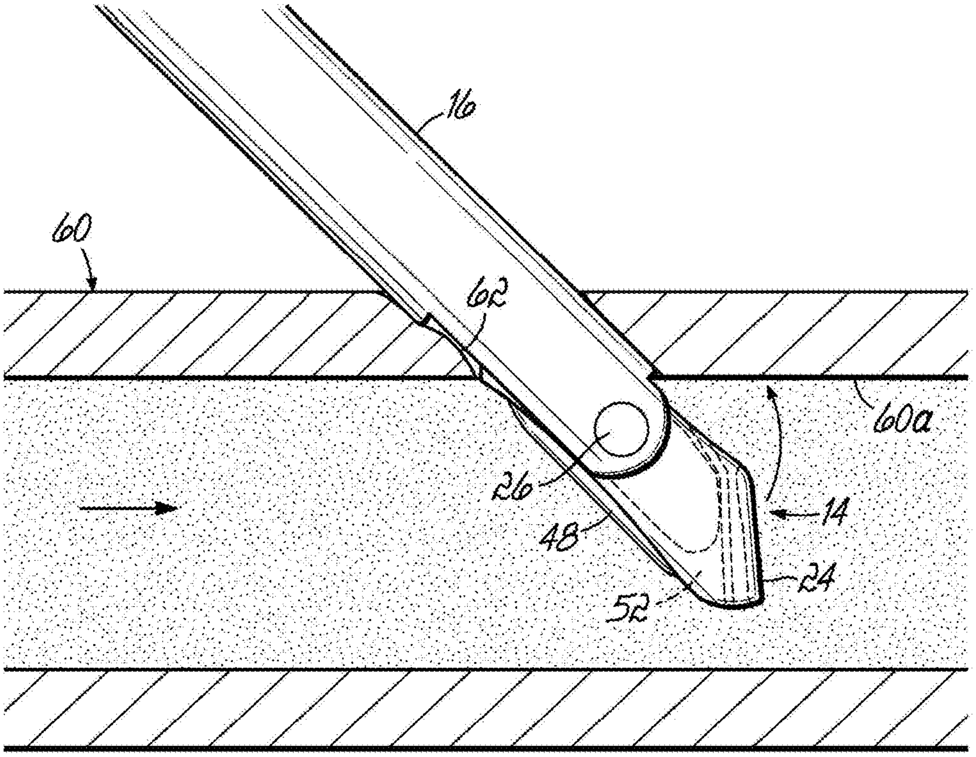
FIGS. 7A through 7I schematically illustrate the use of the suturing device of FIGS. 1 and 2, and particularly, the distal end and the suturing mechanism within a blood vessel.
Figure 7B:
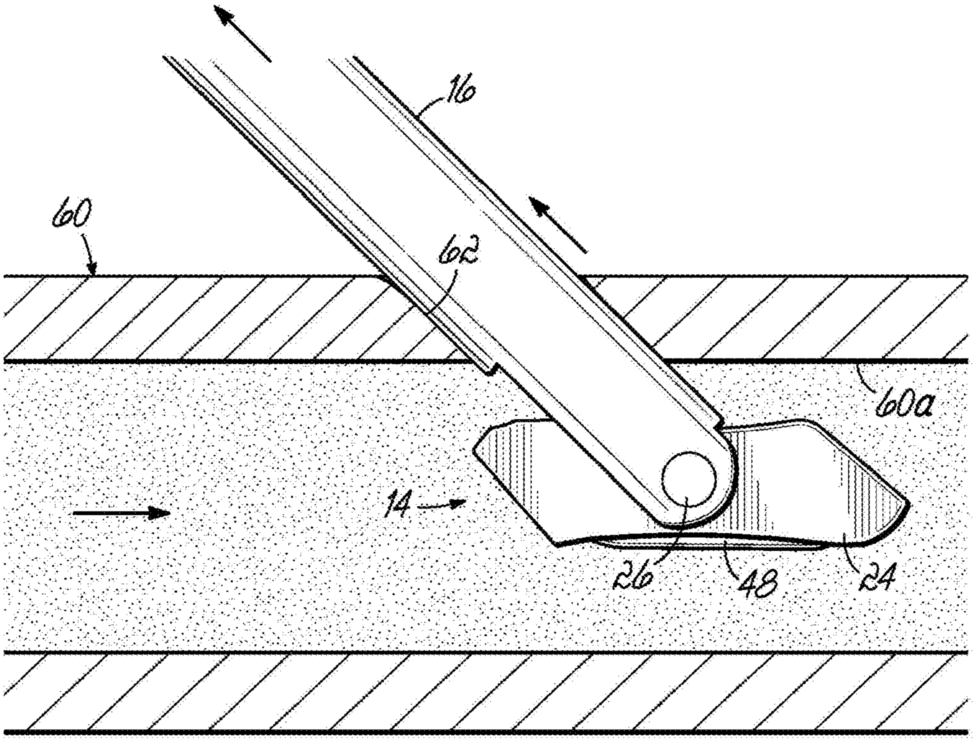
Figure 7C:
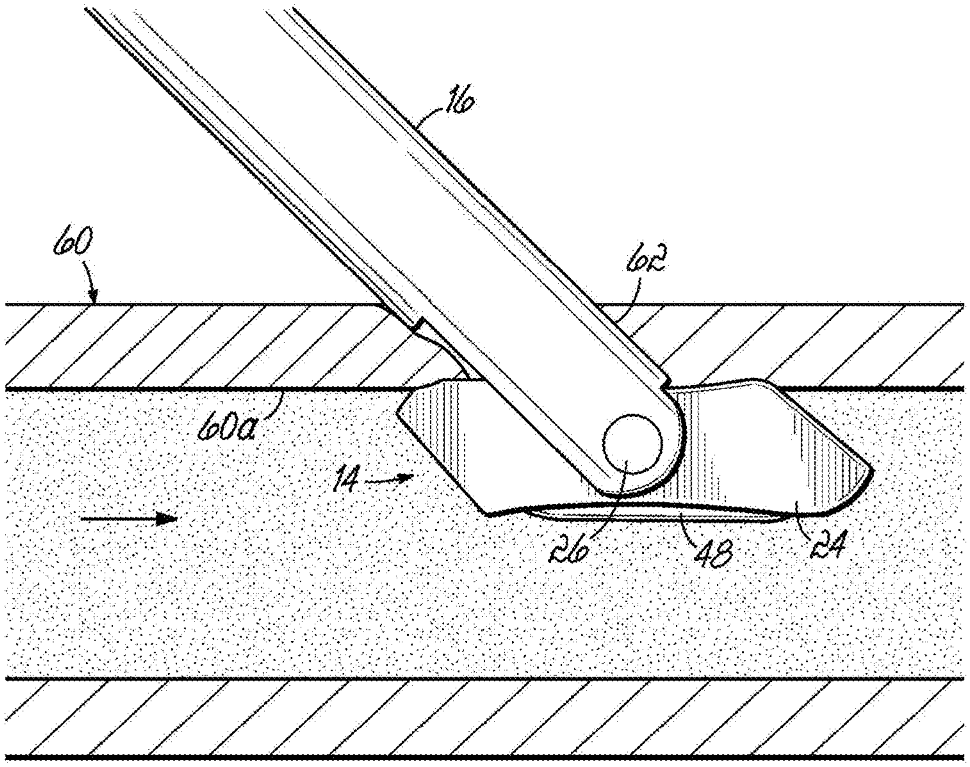
Figure 7D:
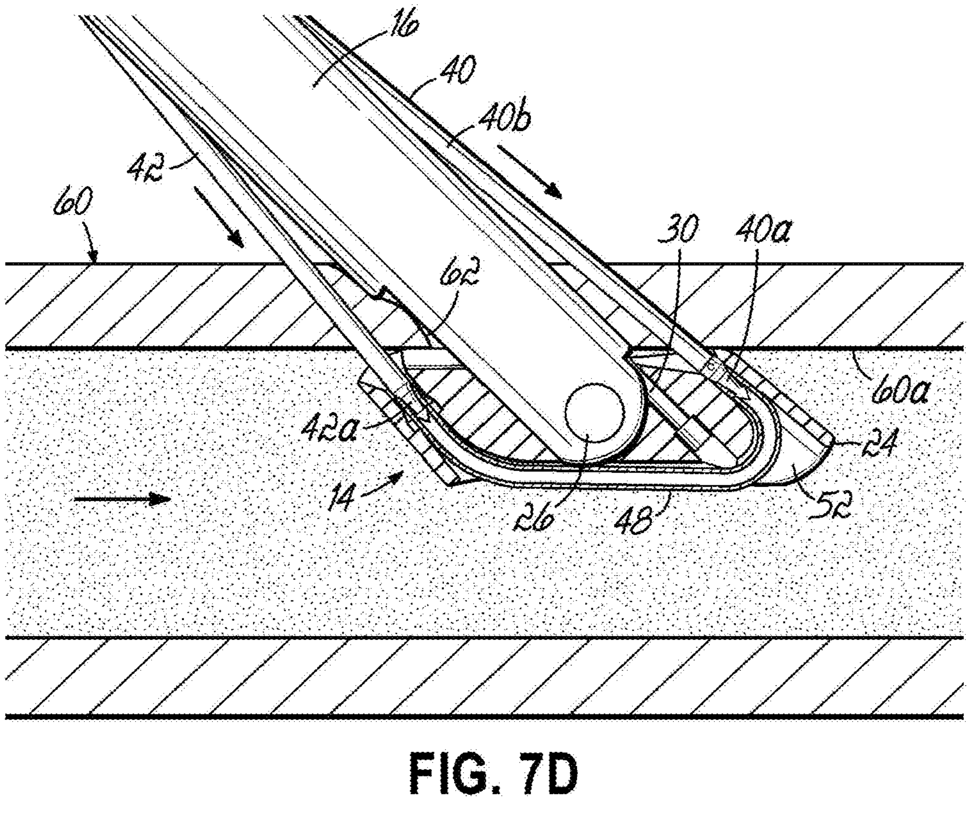
Figure 7E:
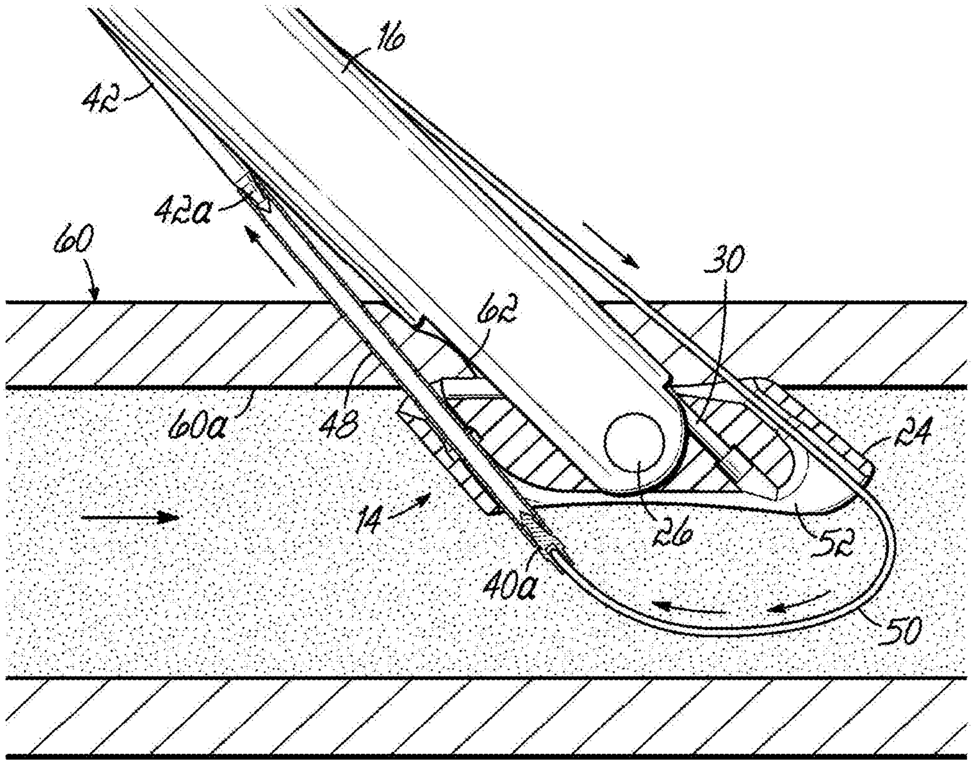
Figure 7F:
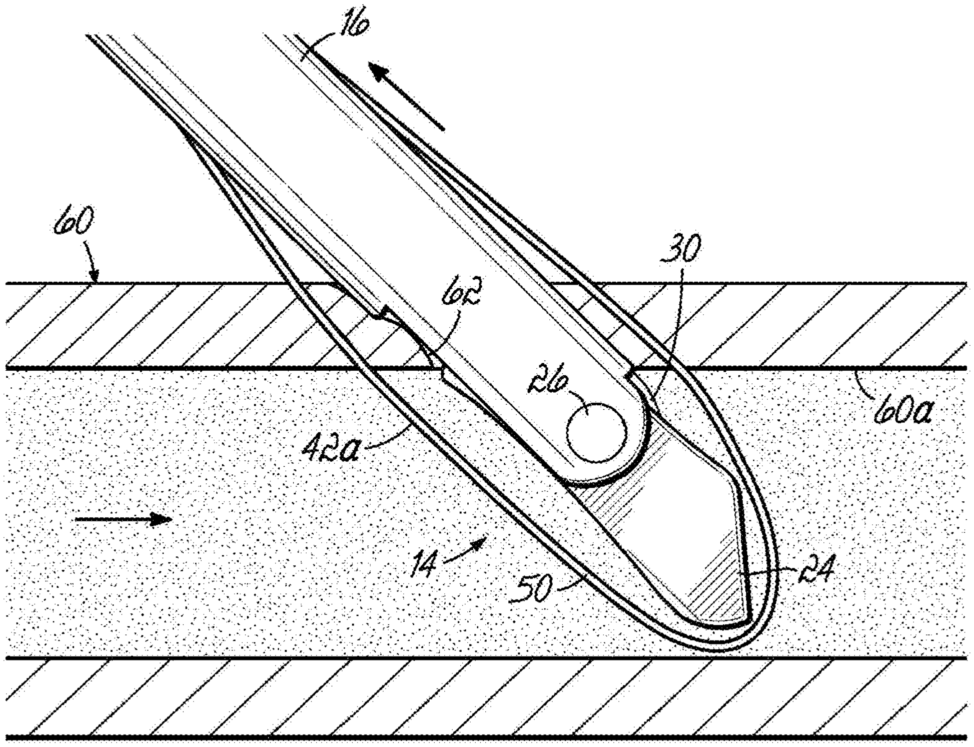
Figure 7G:
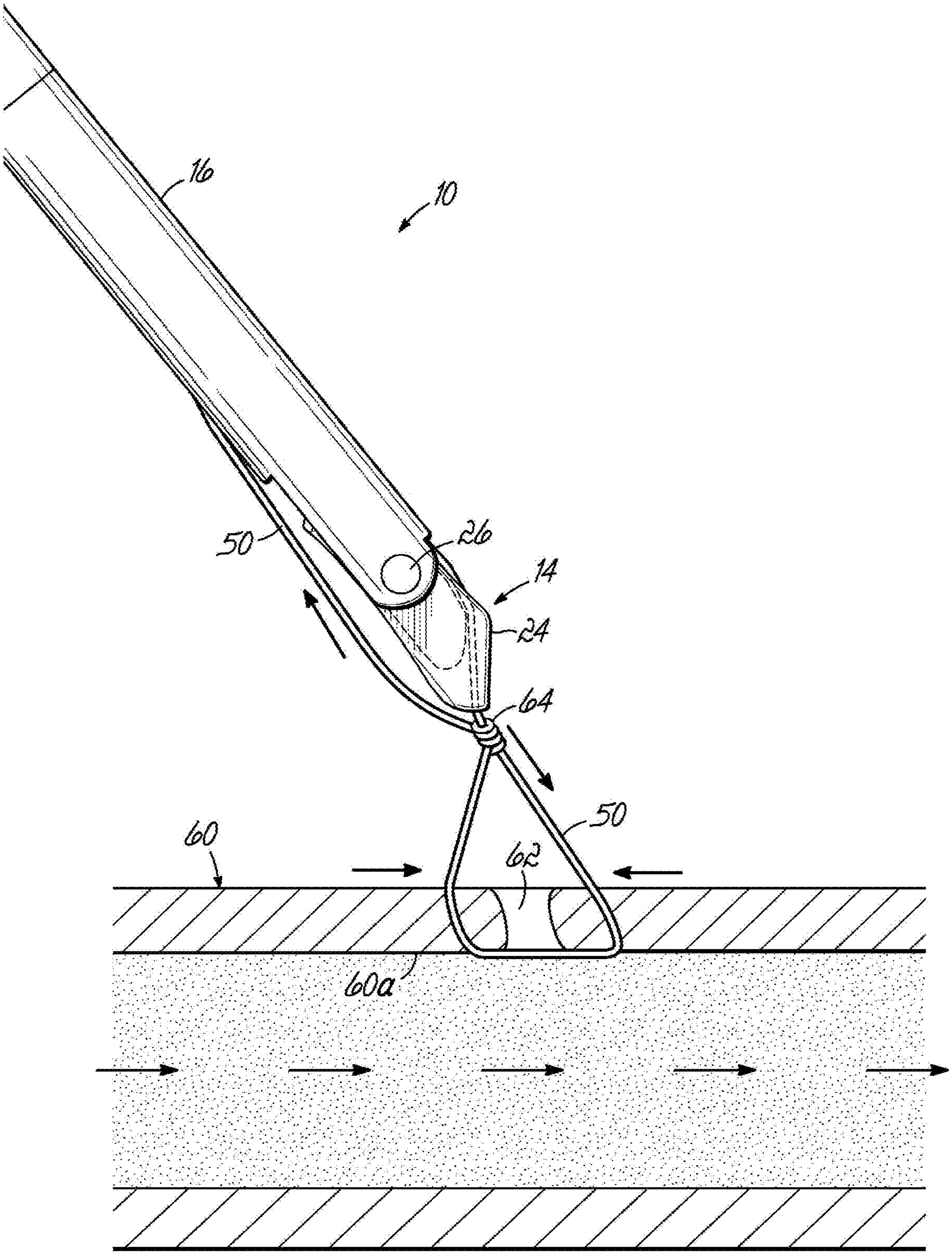
Figure 7H:
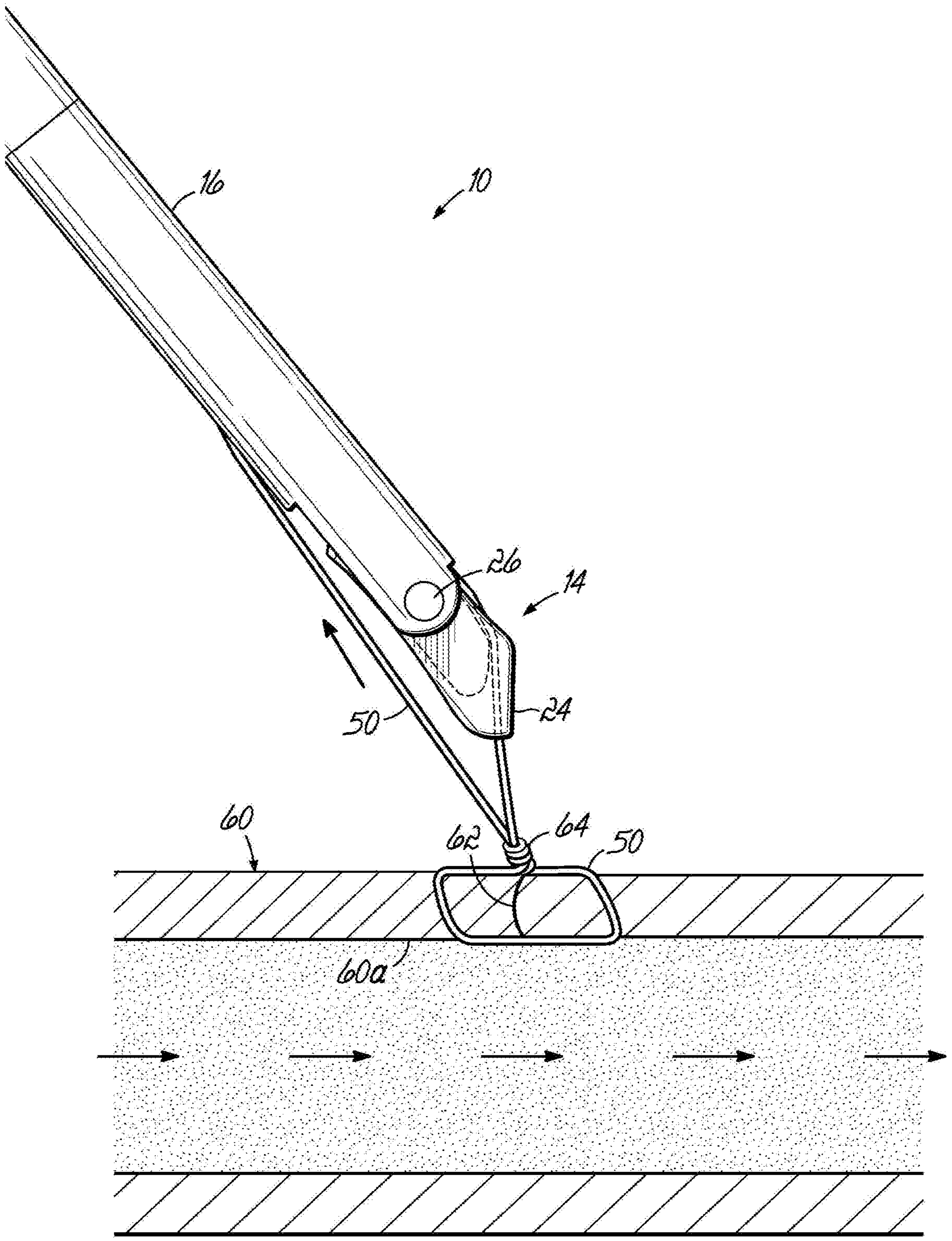
Figure 7I:
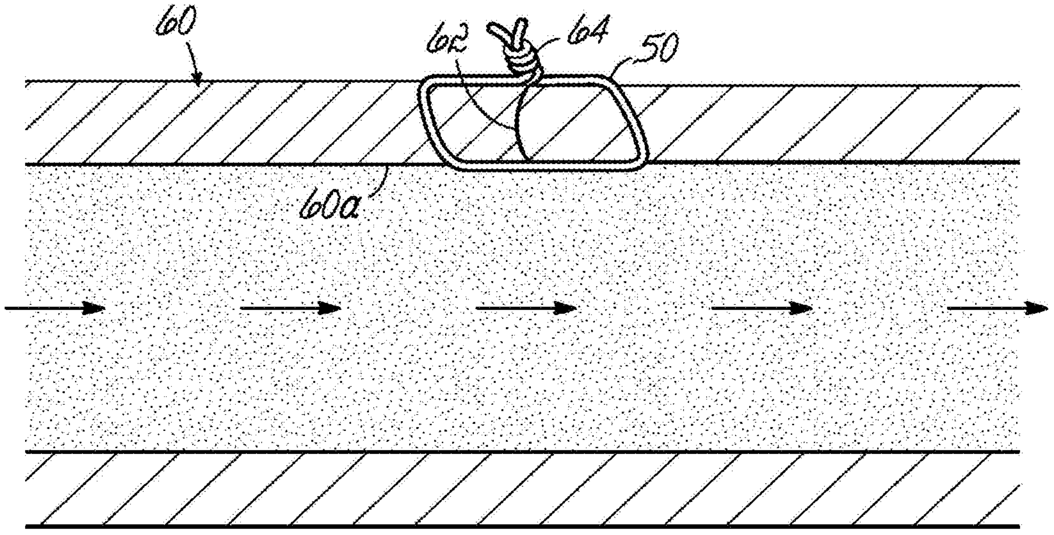

FIGS. 7A through 7I schematically illustrate the use of the device 10 and, particularly, the distal end and the suturing mechanism 14 within a blood vessel 60, such as the common carotid artery, for closing a puncture or opening 62 in a wall of the blood vessel 60. The distal end of the shaft 16, with the pivotal element 24 aligned with its lengthwise extent parallel to and in alignment with the lengthwise axis of the shaft 16, is inserted into the sheath 18 (as described below in connection with FIGS. 8A and 8B). For the sake of simplicity, the sheath is not shown in the FIG. 7 series. The suturing mechanism 14 is activated within the vessel 60 and the pivotal element 24 is pivoted into the angled position relative to the lengthwise axis of the shaft 16 as shown in FIG. 7B by moving the slide actuator 20 as previously described. The pivotal element 24 is then pulled proximally against the interior of the vessel wall 60*a* by slightly pulling proximally on the device 10 and therefore the shaft 16 as shown in FIG. 7C. Once the pivoted element 24 is in this position, the needles 40, 42 are deployed or moved distally as previously described by depressing plunger 22 (see FIGS. 4A, 4B and 5A, 5B) such that the needle tips 40*a*, 42*a* respectively couple with the ends of the flexible coupling member 48 as shown in FIG. 7D. Needle body 40*b* and needle 42 are retracted proximally by releasing plunger 22 as shown and described in connection with FIGS. 5A, 5B, 6A and 6B. This causes the needle tip 40*a* to detach from the needle body 40*b* while leaving the tensile element or suture 50 fixed to the needle tip 40*a* and the needle tip 40*a* still fixed to the flexible coupling member 48. Pulling rearwardly or proximally on the integral needle 42 by further retracting or pulling on the proximal plunger portion 22*a* (see FIG. 6A) will then pull both the flexible coupling member 48 and the needle tip 40*a* and connected tensile element or suture 50 through the vessel wall 60*a* adjacent the puncture or opening 62 as shown progressively in FIGS. 7E and 7F. The pivotal element 24 is then actuated into its original aligned orientation as previously described for allowing the device 10 and, particularly, the distal end of the shaft 16 and the suturing mechanism 14 to be pulled proximally and removed from the blood vessel 60. As further shown in FIGS. 7G and 7H, a suture knot 64 is deployed from the shaft 16, such as through the needle body 40*b* if it is hollow (see FIG. 6B), or through a lumen in the shaft 16. However, the suture knot 64 will preferably deploy from the other needle 42, with the "coils" of the knot 64 wrapped around the needle 42. Alternatively, the tensile element or suture 50 and suture knot 64 may be located outside of the shaft 16. The suture knot 64 may be any desired form of knot suitable for tying off a suture, such as the type that will automatically tighten as one end of the tensile element or suture 50 is pulled. One form of knot suitable for use in this situation is the "Tennessee Slider" knot. The knot 64 is tightened against the outside of the vessel 60 as shown in FIG. 7I to fully approximate or close the opening 62.

Figure 8A:
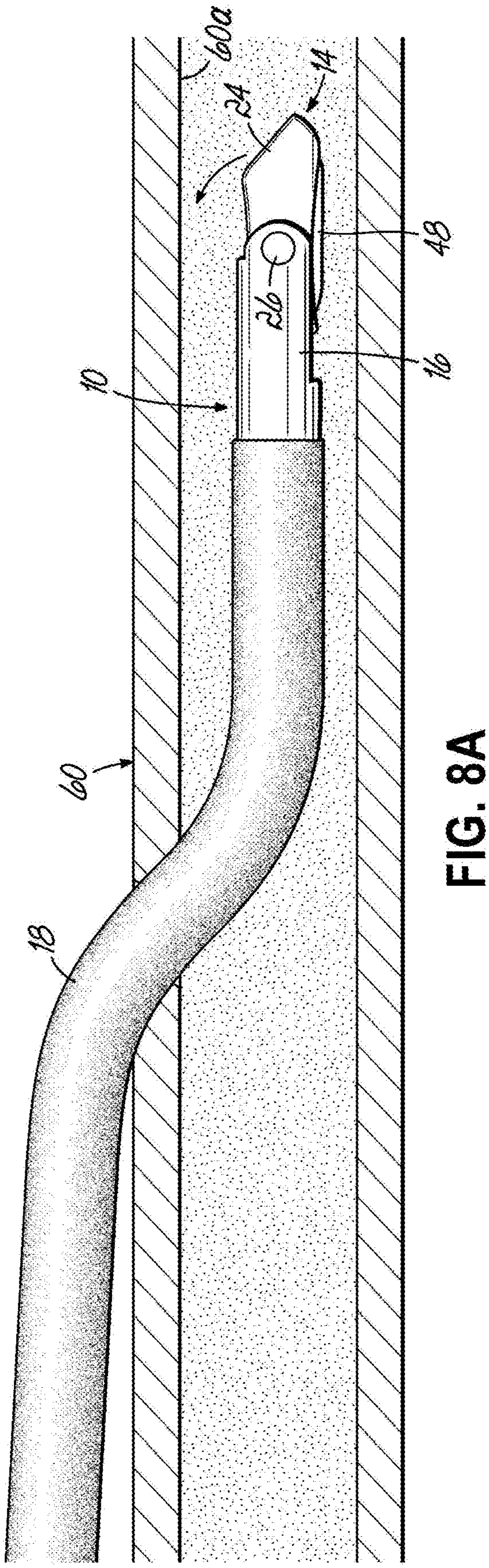
FIGS. 8A and 8B illustrate the suturing device exchanged internally with the introducer sheath while within a blood vessel.
Figure 8B:
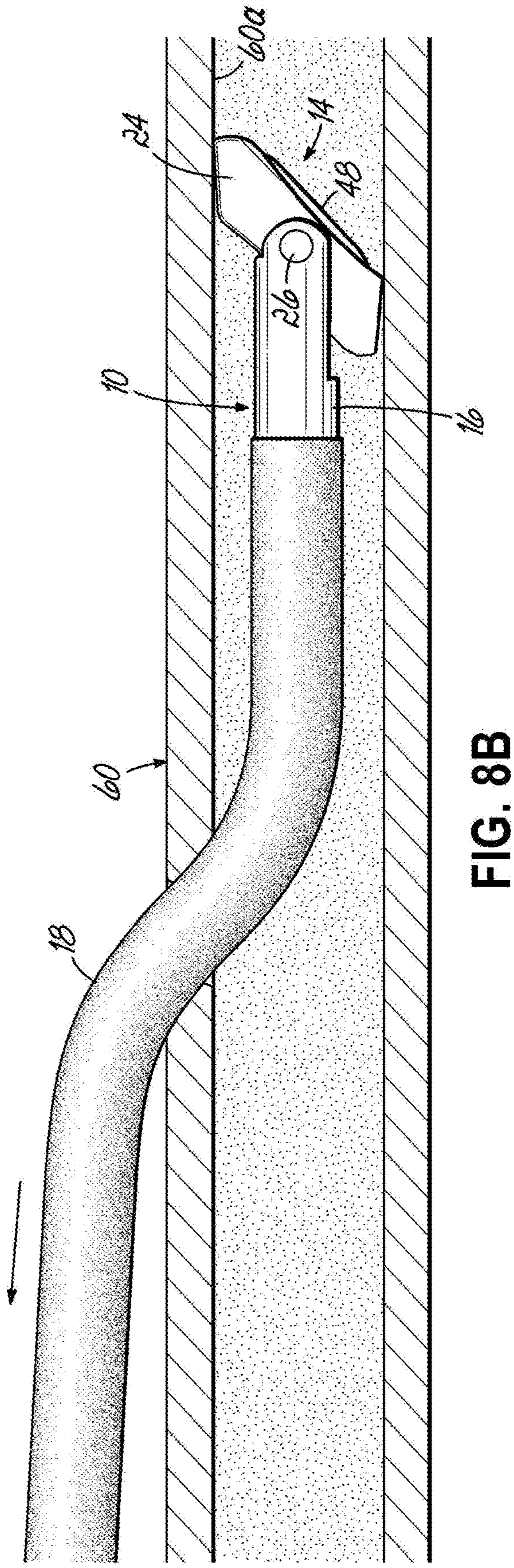

FIGS. 8A and 8B illustrate how the device 10 is exchanged internally with the introducer sheath 18 while within the blood vessel 60. The device 10 is inserted into the blood vessel 60 prior to the removal of the introducer sheath 18. Depth markers or indicators on the outer surface of the device 10 can give visual feedback to the doctor as to how far to insert the device 10 into the introducer sheath 18. The pivotal element 24 is actuated into its angled, transverse orientation as previously described (FIG. 8B). The introducer sheath 18 and the device 10/shaft 16 are pulled proximally out of the vessel 60 until the angled pivotal element 24 contacts the inner wall surface 60*a* (best depicted in FIG. 7C). The introducer sheath 18 is then pulled rearward or proximally along the shaft 16 while the suturing mechanism 14 remains within the vessel 60. The introducer sheath 18 remains in surrounding relation to the shaft 16 for the remainder of the procedure. The device 10 is then ready for the deployment of the suture needles 40, 42 and the remainder of the procedure as described herein.

Figure 9A:
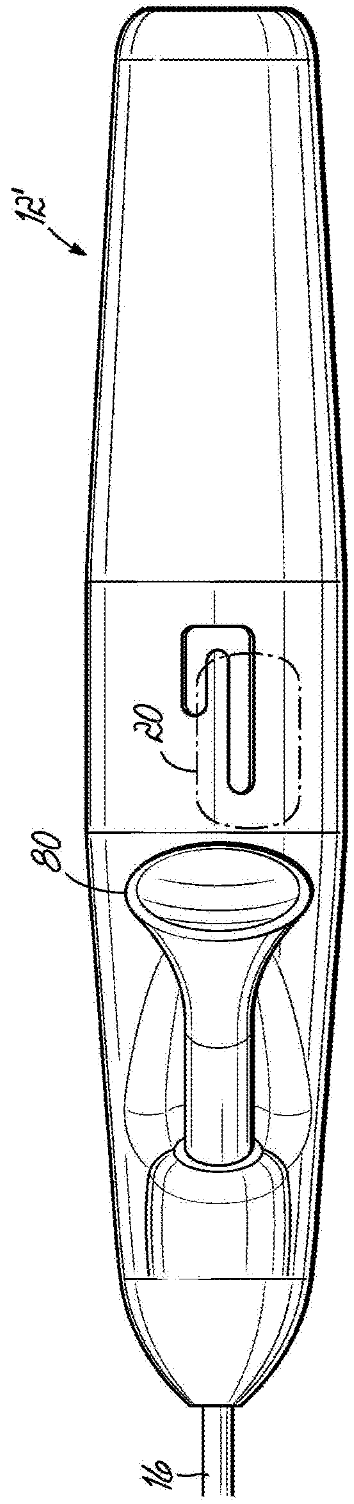
FIGS. 9A and 9B illustrate a first alternative embodiment of a handle.
Figure 9B:
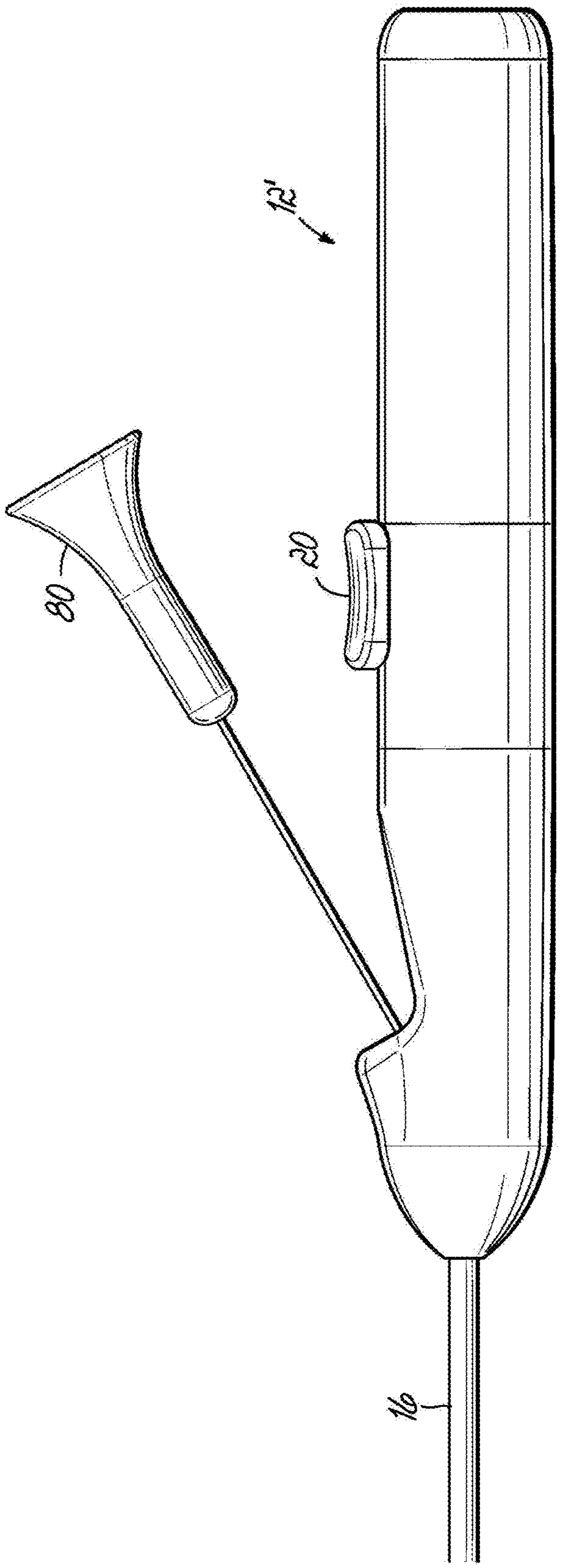

FIGS. 9A and 9B illustrate an alternative embodiment for a handle 12'. Specifically, handle 12' locates a plunger element 80 on the top of the handle 12' as opposed to locating it at the proximal end as illustrated in the first embodiment illustrated in FIG. 1. The pivotal element 24 is moved or actuated with the slide actuator 20 as previously described. In this embodiment the two-piece needle 40 may also be actuated by movement of the slide actuator 20. Spring-biased movement of the slide actuator 20 rearwardly or in a proximal direction will then both re-orient the pivotal element 24 into its aligned orientation parallel to the shaft 16 and remove the needle body 40*b* from the blood vessel 60. Actuation and de-actuation (i.e., distal and proximal movement) of the needle 42 occurs with the plunger 80. Full depression of the plunger 80 shown in FIG. 9A actuates the needle 42 (i.e. moves the integral needle 42 in a distal direction coupling it to the flexible coupling member 48), while de-actuation or movement of the needle 42 in the proximal direction occurs when the plunger 80 is moved away from the handle 12' as shown in FIG. 9B. The needle 42 is removed from the blood vessel 60 creating a loop of tensile element or suture 50 as previously described.

Figure 10A:
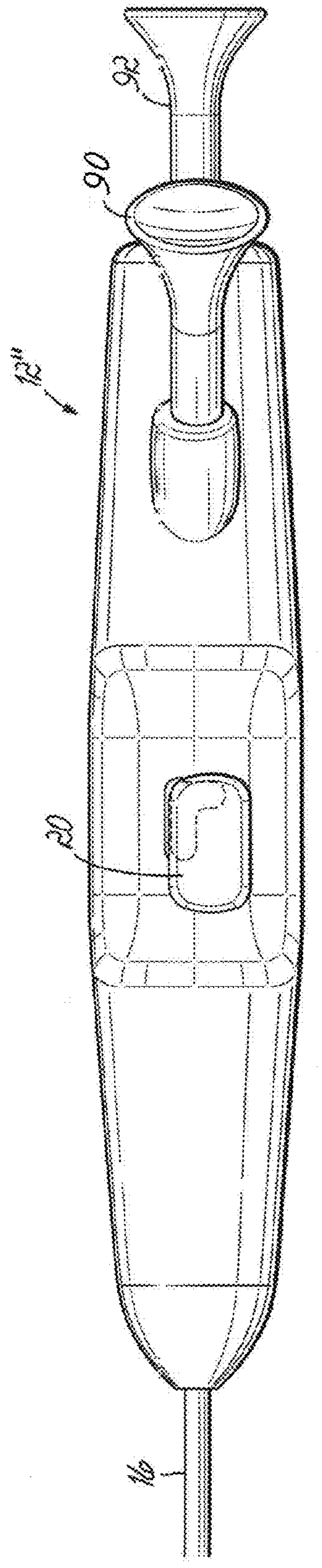
FIGS. 10A and 10B illustrate a second alternative embodiment of a handle.
Figure 10B:
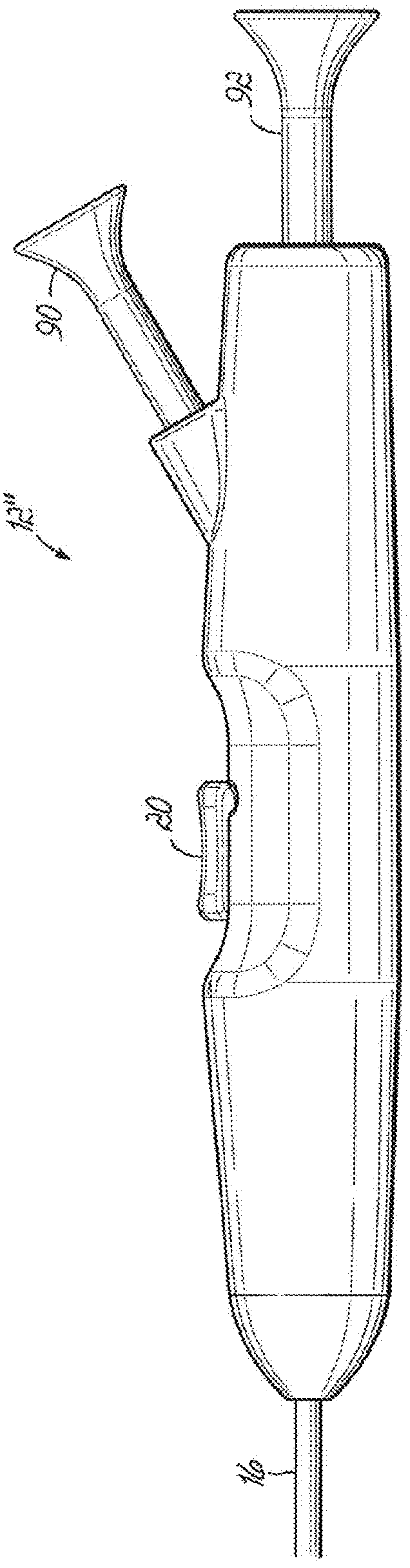

FIGS. 10A and 10B illustrate another alternative embodiment for a handle 12". Specifically, handle 12" utilizes separate actuators in the form of plungers 90, 92 for respectively actuating or moving the two-piece needle 40 and the integral needle 42. A slide actuator 20 is provided for actuating or moving the pivotal element 24 as previously described. However, in this embodiment, the needles 40, 42 may be actuated in a staged manner with one needle being actuated before the other in either or both directions depending on the needs or desires of the user. The two-piece needle 40 may be actuated and automatically de-actuated by the plunger 90 located on top of the handle 12", while the integral needle 42 may be actuated and automatically de-actuated by the plunger 92 located at the rear of the handle 12". The procedure generally may otherwise follow the method or methods described herein.

Figure 11A:
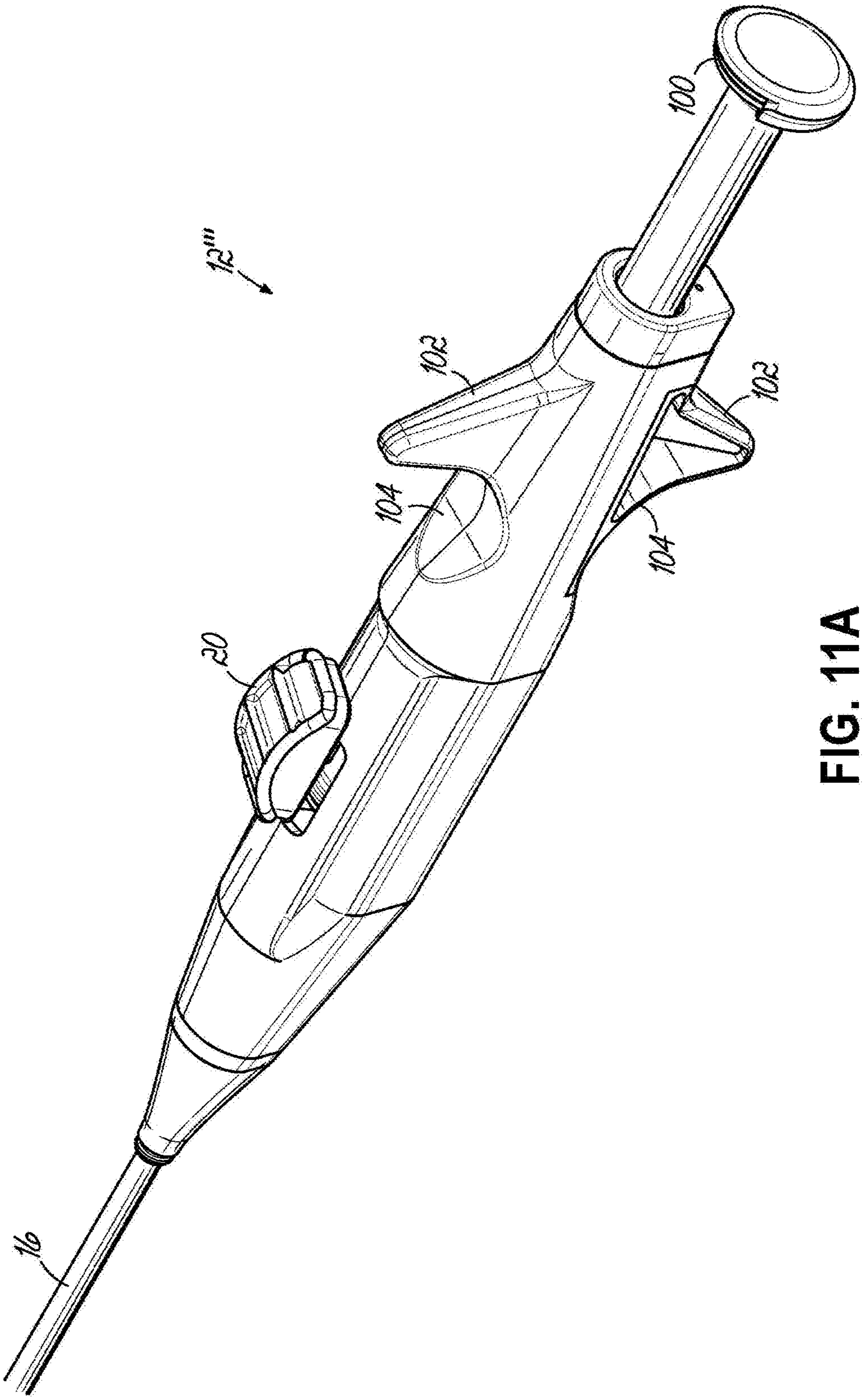
FIGS. 11A and 11B illustrate a third alternative embodiment of a handle.
Figure 11B:
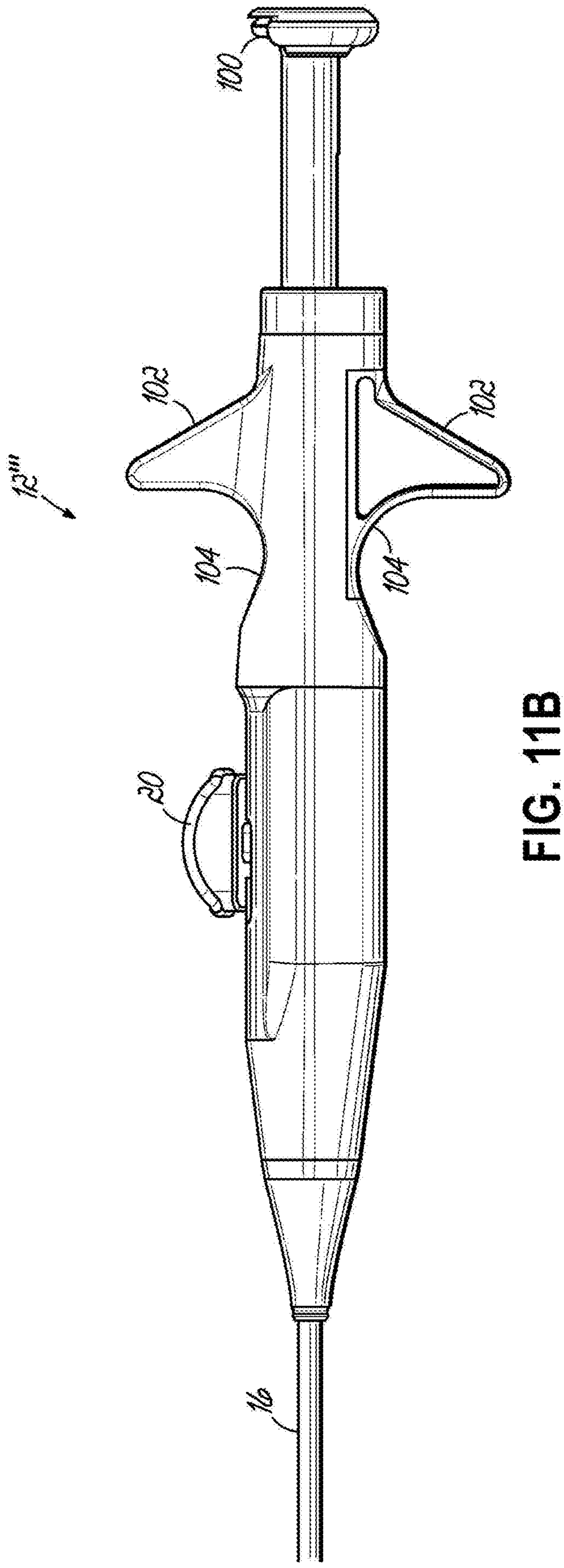

FIGS. 11A and 11B illustrate an alternative embodiment for a handle 12". Specifically, handle 12'" includes an alternate plunger element 100 and a pair of tabs 102 on the top and bottom of the handle 12". The pivotal element 24 is moved or actuated with the slide actuator 20 as previously described. In this embodiment the two-piece needle 40 may also be actuated by movement of the slide actuator 20. Spring-biased movement of the slide actuator 20 rearwardly or in a proximal direction will then re-orient the pivotal element 24 into its aligned orientation parallel to the shaft 16. Actuation and de-actuation (i.e., distal and proximal movement) of the needle 42 occurs with the plunger 100. Full depression of the plunger 100 in the distal direction actuates the needles 40, 42 (i.e. moves the integral needle 42 in a distal direction coupling it to the flexible coupling member 48), while de-actuation or movement of the needle 42 in the proximal direction occurs when the plunger 100, with spring-biased movement, withdraws the needles 40, 42 in the proximal direction. Needles 40, 42 are removed from the blood vessel 60 creating a loop of tensile element or suture 50 as previously described.

The tabs 102 are aligned along the longitudinal axis of the generally cylindrical body of the handle 12" and are positioned approximately opposite each other on the top and bottom of the handle 12''' as shown in FIGS. 11A and 11B. The tabs 102 include concave radiused portions 104. The radiused portions 104 are configured to accommodate a user's fingers. The tabs 102 may be configured or positioned on the handle 12" so that a user may engage each of the tabs 102 with at least one finger and depress the plunger 100 with the user's thumb of the same hand thereby allowing the user's other hand to perform other functions, for example. The tabs 102 may be positioned in alternate orientations, such as on the sides of the handle 12", for example. Referring to the longitudinal axis of the handle 12", the tabs 102 may be positioned in other orientations anywhere between 120° to 180° from each other for improved ergonomics. The tabs 102 may be positioned in a staggered configuration along the length of the handle 12" such that one tab 102 may be located forward of the other tab 102 for improved ergonomics. Tabs 102 may be the same size and shape or vary in shape and size to improve ergonomics.

While the present invention has been illustrated by the description of specific embodiments thereof, and while the embodiments have been described in considerable detail, it is not intended to restrict or in any way limit the scope of the appended claims to such detail. The various features described herein may be used alone or in any combination within and between the various embodiments. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A method of closing an opening in a vessel, the method comprising:

directing a suturing mechanism, the suturing mechanism including a pivotal element and being coupled to a distal end of an elongate shaft, through the opening and into the vessel;

activating the pivotal element into a deployed orientation after the suturing mechanism is positioned within an interior of the vessel;

directing a first needle through a vessel wall adjacent to the opening and coupling the first needle to a first end of a coupling member;

directing a tensile member coupled to the first needle through the vessel wall adjacent to the opening using the first needle;

directing a second needle through the vessel wall adjacent to the opening and coupling the second needle to a second end of the coupling member;

retracting the first needle from the vessel wall;

retracting the second needle from the vessel wall;

pulling the tensile member through the vessel wall adjacent to the opening using the coupling member;

deactivating the pivotal element;

withdrawing the suturing mechanism from the vessel; and tightening the tensile member to close and seal the opening.

2. The method of claim 1, wherein the vessel further comprises a blood vessel, and the method further comprises:

directing a portion of an introducer sheath through the opening and into the blood vessel;

directing the suturing mechanism through the introducer sheath and into the blood vessel; and withdrawing the introducer sheath from the blood vessel with the suturing mechanism remaining in the blood vessel thereby inhibiting blood from exiting the blood vessel through the opening.

3. The method of claim 1, wherein the deployed orientation is an angled orientation.

4. The method of claim 1, wherein the coupling member comprises a flexible coupling member.

5. The method of claim 1, wherein the first needle includes a first needle body and a detachable tip coupled to the tensile member; and wherein the method further comprises:

coupling the detachable tip to the first end of the coupling member, detaching the detachable tip from the first needle body, and pulling the detachable tip through the vessel wall adjacent to the opening using the coupling member.

* * * * *